(12) United States Patent
Tanizawa et al.

(10) Patent No.: US 6,197,225 B1
(45) Date of Patent: Mar. 6, 2001

(54) CHROMENE COMPOUND

(75) Inventors: Tsuneyoshi Tanizawa; Tadashi Hara; Yuichiro Kawabata; Junji Momoda; Hironobu Nagoh, all of Tokuyama (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 09/242,598

(22) PCT Filed: Jun. 18, 1998

(86) PCT No.: PCT/JP98/02724
§ 371 Date: Feb. 19, 1999
§ 102(e) Date: Feb. 19, 1999

(87) PCT Pub. No.: WO98/57943
PCT Pub. Date: Dec. 23, 1998

(30) Foreign Application Priority Data

Jun. 19, 1997 (JP) .................................................. 9-162541
Aug. 1, 1997 (JP) .................................................. 9-207871
Mar. 30, 1998 (JP) .................................................. 10-84678

(51) Int. Cl.[7] .......................... G02B 5/23; C07D 311/92
(52) U.S. Cl. .......................... 252/586; 549/389; 549/331; 549/60; 549/58; 548/525
(58) Field of Search .......................... 252/586; 549/389, 549/331, 60, 58; 548/525; 351/163

(56) References Cited

U.S. PATENT DOCUMENTS

| | | | |
|---|---|---|---|
| 5,395,566 | * 3/1995 | Kobayakawa et al. | 252/586 |
| 5,623,005 | * 4/1997 | Rickwood et al. | 252/586 |
| 5,658,501 | * 8/1997 | Kumar et al. | 252/586 |
| 5,808,100 | * 9/1998 | Momoda et al. | 252/586 |
| 6,096,246 | * 8/2000 | Chan et al. | 252/586 |

FOREIGN PATENT DOCUMENTS

| | | |
|---|---|---|
| 0246114 | 11/1987 | (EP). |
| 2762840 | 11/1998 | (FR). |
| 6-306354 | * 11/1994 | (JP). |
| 95/16215 | * 6/1995 | (WO). |

OTHER PUBLICATIONS

Research Disclosure, 36144, May 1994, pp. 267–268.*
B. Van Gemert, et al., "Naphthopyrans. Structural Features and Photochromic Properties", Mol. Cryst. Liq. Cryst. 1997, vol. 297, pp. 131–138.

* cited by examiner

*Primary Examiner*—Philip Tucker

(57) ABSTRACT

A photochromic compound featuring a large fading rate to prevent a change in the color tone at the time of fading, exhibiting little color after aged, and exhibiting good durability in the photochromic property. The photochromic compound is a novel chromene compound having a substituted phenyl group at the second position of the naphthopyrane ring and an alkyl group at the fifth position thereof, and is represented by, for example, the following formula,

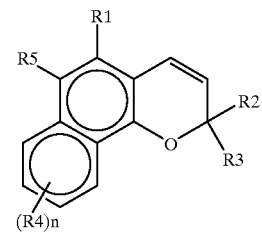

wherein R1 is an alkyl group, R2 and R3 are substituted phenyl groups, and R4 and R5 are substituents.

32 Claims, 1 Drawing Sheet

CHROMENE COMPOUND

TECHNICAL FIELD

The present invention relates to a novel chromene compound which changes into a colored state upon irradiation with light containing ultraviolet rays such as of sunlight or light of a mercury lamp, the change being reversible, and exhibits excellent fading rate as well as excellent durability in the photochromic property, getting little colored even after it is aged. The invention further relates to a photochromic material, to a chromene composition, to a photochromic composition, to a photochromic polymerizable composition and to a photochromic lens, which contain the chromene compound.

BACKGROUND ART

Photochromism is a phenomenon which is drawing attention in these several years, and stands for a reversible action of a compound; i.e., a compound quickly changes its color when it is irradiated with light containing ultraviolet rays such as of sunlight or light of a mercury lamp, and resumes its initial color when it is no longer irradiated with light and is placed in a dark place. The compound having such a property is called photochromic compound. Though a variety of compounds have heretofore been synthesized, no common feature is particularly recognized among their structures.

U.S. Pat. No. 4,980,089 discloses a chromene compound represented by the following formula (A),

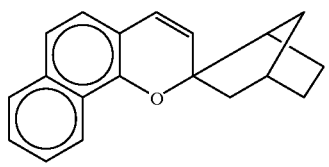

(A)

This chromene compound exhibits photochromic properties near room temperature (20 to 30° C.) but exhibits a slow fading rate when it is placed in a dark place after it has developed a color upon being irradiated with ultraviolet rays. When the colors are mixed upon being combined with photochromic compounds having other color tones, such as a fulgimide and a spirooxazine having relatively fast fading rates, the hue changes when the colors fade.

Furthermore, PCT Unexamined Patent Publication WO95/16215 discloses a chromene compound represented by the following formula (B),

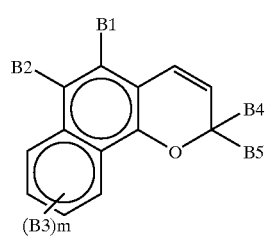

(B)

wherein B1 is an aminocarbonyl group or an alkoxycarbonyl group, B2 and B3 are hydrogen atoms, alkyl groups, substituted or unsubstituted phenyl groups or alkoxyl groups, m is from 0 to 3, B4 and B5 are substituted or unsubstituted aryl groups, substituted or unsubstituted heteroaryl groups, substituted or unsubstituted adamantylidene groups, or substituted or unsubstituted norbornylidene groups.

This compound exhibits an increased fading rate compared to the compound disclosed in the above U.S. Pat. No. 4,980,089 but is not still capable of completely preventing a change in the hue when the mixed colors fade. When aged, furthermore, this compound is more colored than when the compound (A) is aged.

PCT Unexamined Patent Publication WO95/16215 further discloses, as a comparative example, a compound represented by the following formula (C),

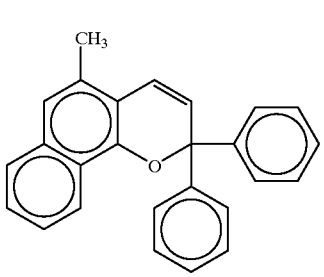

(C)

exhibiting, however, a fading rate nearly the same as that of the above-mentioned compound (A).

As described above, the conventional chromene compounds are not still satisfactory with respect to the fading rate and the color after they are aged.

DISCLOSURE OF THE INVENTION

The object of the present invention therefore is to provide a chromene compound which exhibits improved photochromic property, increased fading rate, and is little colored after it is aged and exhibits excellent durability in the photochromic property compared with those of the conventional chromene compounds.

The present invention was proposed in order to accomplish the above-mentioned object, and is concerned with a chromene compound in which the fifth position of a naphthopyrane ring is substituted by an alkyl group. The chromene compound of the present invention exhibits a large fading rate, permits the hue to change little when the mixed colors are to be faded, is little colored after it is aged, and exhibits excellent durability in the photochromic property.

That is, the present invention is concerned with a chromene compound represented by the following general formula (1),

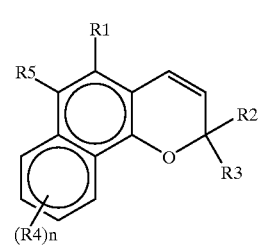

(1)

wherein

R1 is an alkyl group in which a carbon atom bonded to a naphthopyrane ring is a primary carbon atom, a secondary carbon atom or a tertiary carbon atom, R2 and R3 are substituted or unsubstituted aryl groups or substituted or unsubstituted heteroaryl groups which may be different from each other, or R2 and R3 may be coupled to each other to form a substituted or unsubstituted adamantane ring, a substituted or unsubstituted bicyclononane ring, or a substituted or unsubstituted norbornane ring, R4 is a substituent, n is an integer of 0 to 4 representing the number of the substitutents R4 and, when n is 2 or larger, R4 may be the same or different substituents, R5 is a hydrogen atom or a substituent, and wherein when R1 is an alkyl group in which a carbon atom bonded to the naphthopyrane ring is a primary carbon atom, R2 and R3 may be each a group represented by the following formula (2),

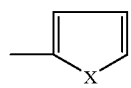

(2)

wherein X is an oxygen atom or a sulfur atom, or a group represented by the following formula (3),

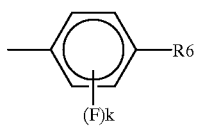

(3)

wherein R6 is an alkoxyl group or a trifuloromethoxy group, and k is 0 or 1, and R2 and R3 may be different from each other, and at least either R2 or R3 is a group represented by the above formula (3), and R5 is a hydrogen atom.

Other inventions are concerned with a chromene composition containing a chromene compound represented by the above-mentioned general formula (1) and other chromene compounds; a photochromic composition containing a chromene compound represented by the above-mentioned general formula (1), other chromene compounds, a spirooxazine compound and a fulgimide compound; a photochromic polymerizable composition containing a polymerizable monomer and the compositions; and a photochromic lens obtained by curing the photochromic polymerizable composition.

BEST MODE FOR CARRYING OUT THE INVENTION

Figure 1:
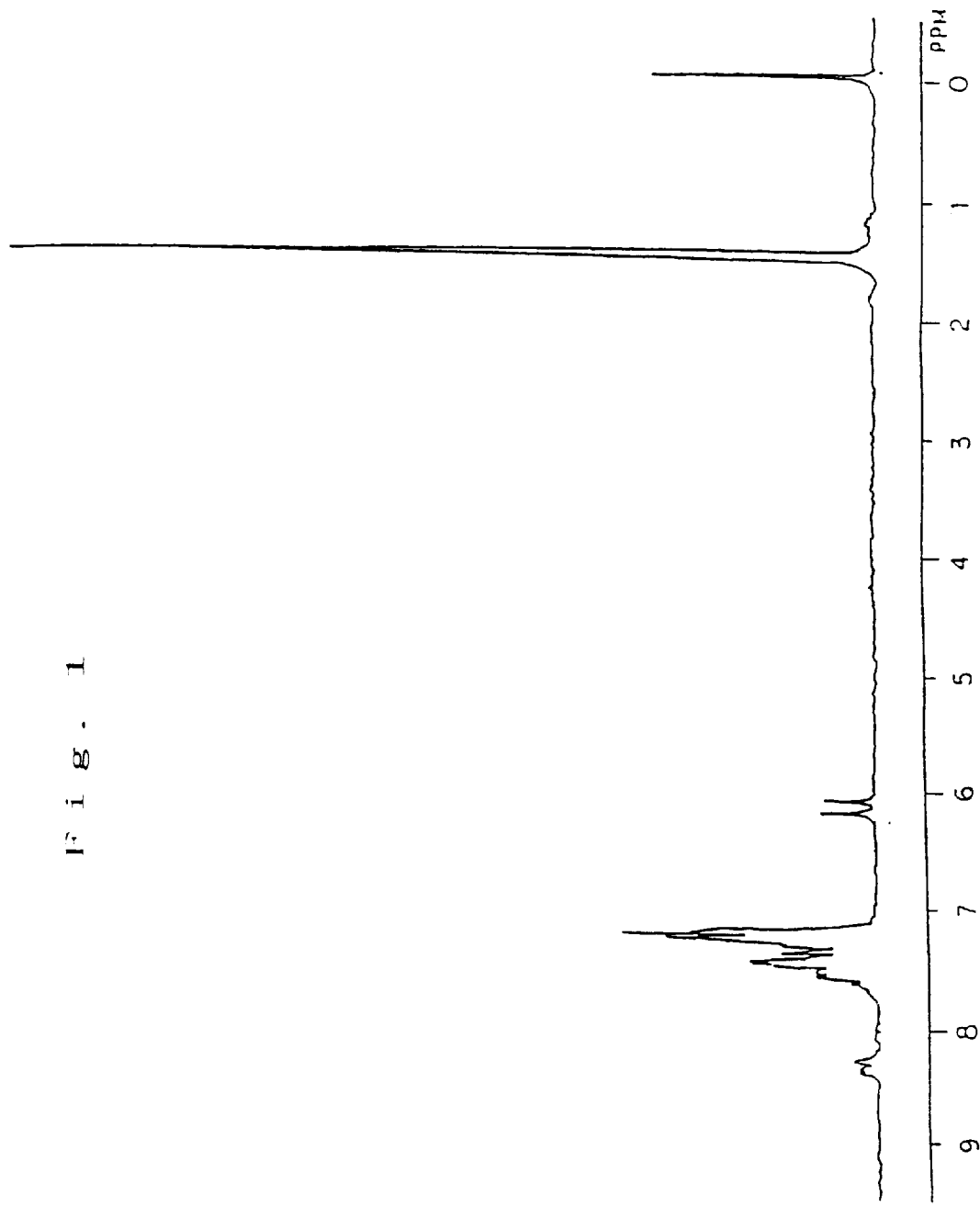
FIG. 1 is a diagram of a proton nuclear magnetic resonance spectrum of a chromene compound of Example 1.

In the present invention, it is important that an alkyl group is substituted for carbon at the fifth position of a naphthopyrane ring. With the alkyl group being substituted for a carbon atom at the fifth position of the naphthopyrane ring, the compound of the invention exhibits a fading rate larger than that of the conventional chromene compounds.

In the general formula (1), R1 is an alkyl group. The alkyl group R1 may be the one in which a carbon atom bonded to the naphthopyrane ring is a primary carbon atom or the one in which a carbon atom bonded to the naphthopyrane ring is a secondary carbon atom or a tertiary carbon atom.

There is no particular limitation on the alkyl group in which a carbon atom bonded to the naphthopyrane ring is a primary carbon atom provided it is the alkyl group in which a carbon atom directly bonded to the naphthopyrane ring is a primary carbon atom. Other carbon atoms such as a carbon atom bonded to the primary carbon atom or the succeeding carbon atoms may be primary carbon atoms, secondary carbon atoms or tertiary carbon atoms. Among such alkyl groups, the alkyl group having 1 to 4 carbon atoms is preferred from the standpoint of yield of synthesis. Preferred examples of the alkyl group in which a carbon atom bonded to the naphthopyrane ring is a primary carbon atom include methyl group, ethyl group, n-propyl group and n-butyl group. Among them, the methyl group and the ethyl group are particularly preferred from the standpoint of easy synthesis.

There is no particular limitation on the alkyl group in which a carbon atom bonded to the naphthopyrane ring is ada secondary carbon atom or a tertiary carbon atom provided it is the alkyl group in which a carbon atom directly bonded to the naphthopyrane ring is a seconary carbon atom or a tertiary carbon atom. Other carbon atoms such as a carbon atom bonded to the secondary carbon atom or the tertiary carbon atom or the succeeding carbon atoms may be primary carbon atoms, secondary carbon atoms or tertiary carbon atoms. Among such alkyl groups, the alkyl group having 3 to 15 carbon atoms and, particularly, 3 to 6 carbon atoms is preferred. Preferred examples of the alkyl group in which a carbon atom bonded to the naphthopyrane ring is a secondary carbon atom or a tertiary carbon atom include isopropyl group, sec-butyl group, t-butyl group, iso-butyl group and t-amyl group. Among them, the isopropyl group and the t-butyl group are particularly preferred from the standpoint of easy synthesis.

In the above-mentioned general formula (1), R2 and R3 are substituted or unsubstituted aryl groups or substituted or unsubstituted heteroaryl groups which may be different from each other. Or, R2 and R3 may be coupled to each other to form a substituted or unsubstituted adamantane ring, a substituted or unsubstituted bicyclononane ring, or a substituted or unsubstituted norbornane ring.

Though there is no particular limitation on the substituted or unsubstituted aryl group, it is desired that the aryl group has 6 to 14 carbon atoms. Concrete examples of the aryl group include phenyl group, naphthyl group and tolyl group.

Though there is no particular limitation on the substituent of the substituted or unsubstituted aryl group, preferred examples of the substituent include alkyl group, alkoxyl group, trifluoromethoxy group, aralkyl group, alkylcarbonyl group, alkoxycarbonyl group, cyano group, substituted amino group, substituted or unsubstituted heterocyclic group having nitrogen atom as a hetero atom and is substituted or is not substituted by the nitrogen atom, or a condensed heterocyclic group formed by the condensation of the above heterocyclic group with an aromatic hydrocarbon ring or an aromatic heterocyclic ring, aryl group, acyloxyl group, nitro group, hydroxyl group and halogen atom. The above-mentioned substituents will now be described.

There is no particular limitation on the above-mentioned alkyl group. Generally, however, it is desired to use an alkyl group having 1 to 10 carbon atoms and, particularly, 1 to 4 carbon atoms from the standpoint of easy synthesis. Concrete examples of the alkyl group include methyl group, ethyl group, n-propyl group, isopropyl group, n-butyl group, sec-butyl group, and t-butyl group.

There is no particular limitation on the alkoxyl group. Generally, however, it is desired to use an alkoxyl group having 1 to 10 carbon atoms and, particularly, 1 to 4 carbon atoms from the standpoint of easy synthesis. Concrete examples of the alkoxyl group include methoxy group, ethoxyl group, n-propoxyl group, isopropoxyl group, n-butoxy group, sec-butoxy group and t-butoxy group.

Though there is no particular limitation on the aralkyl group, it is generally desired to use an aralkyl group having 7 to 16 carbon atoms and, particularly, 7 to 10 carbon atoms from the standpoint of easy synthesis. Concrete examples of the aralkyl group include benzyl group, phenylethyl group, phenylpropyl group and phenylbutyl group.

Though there is no particular limitation on the alkylcarbonyl group, it is generally desired to use an alkylcarbonyl group having 2 to 15 carbon atoms and, particularly, 2 to 7 carbon atoms from the standpoint of easy synthesis. Concrete examples of the alkylcarbonyl group include methylcarbonyl group, ethylcarbonyl group, propylcarbonyl group, isopropylcarbonyl group, n-butylcarbonyl group, t-butylcarbonyl group and benzoyl group.

Though there is no particular limitation on the substituted amino group, it is generally desired to use an amino group having a substituent such as an alkyl group having 1 to 10 carbon atoms or an alkyl group containing a hetero atom. Among them, it is desired to use a substituted amino group having 1 to 5 carbon atoms from the standpoint of easy synthesis. Concrete examples of the substituted amino group include methylamino group, ethylamino group, propylamino group, isopropylamino group, dimethylamino group, diethylamino group, methylethylamino group, 2-hydroxyethylamino group and di-(2-hydroxyethyl)amino group.

There is no particular limitation on the substituted or unsubstituted heterocyclic ring having the nitrogen atom as a hatero atom and in which the nitrogen atom is bonded to the substituted or unsubstituted aryl group or on the condensed heterocyclic ring formed by the condensation of the above heterocyclic ring with an aromatic hydrocarbon ring or an aromatic heterocyclic ring. It is, however, desired that the heterocyclic ring is constituted by 2 to 10 carbon atoms and, more preferably, by 2 to 6 carbon atoms. The ring may include a hetero atom in addition to the nitrogen atom that is bonded to the substituted or unsubstituted aryl group. Not being limited to the nitrogen atom only, furthermore, there may be bonded an oxygen atom, a sulfur atom or a nitrogen atom. As the aromatic hydrocarbon ring or the aromatic heterocyclic ring bonded to the heterocyclic ring, furthermore, there can be exemplified an aromatic hydrocarbon ring or an aromatic heterocyclic ring having 6 to 10 carbon atoms. There can be preferably used a benzene ring, a thiophene ring or a furan ring. As the substituent for the heterocyclic ring or the condensed heterocyclic ring, there can be used an alkyl group having 1 to 4 carbon atoms. Concrete examples of the alkyl group include methyl group, ethyl group, n-propyl group, isopropyl group, n-butyl group, sec-butyl group, and t-butyl group.

Piperidino group, morpholino group, N-methylpiperadinyl group, thiomorpholino group, aziridinyl group and pyrolydinyl group are concrete examples of the substituted or unsubstituted heterocyclic ring having the nitrogen atom as a hetero atom and in which the nitrogen atom is bonded to the substituted or unsubstituted aryl group or of the condensed heterocyclic ring formed by the condensation of the above heterocyclic ring with the aromatic hydrocarbon ring or the aromatic heterocyclic ring.

Though there is no particular limitation on the aryl group, it is generally desired to use an aryl group having 6 to 20 carbon atoms and, particularly, 6 to 14 carbon atoms from the standpoint of easy synthesis. Concrete examples Of the aryl group include phenyl group, naphthyl group and tolyl group.

Though there is no particular limitation on the acyloxyl group, it is generally desired to use an acyloxyl group having 1 to 15 carbon atoms and, particularly, 2 to 7 carbon atoms from the standpoint of easy synthesis. Concrete examples of the acyloxyl group include acetoxyl group, propionyloxy group, benzoyloxy group and (meth)acryloyloxy group.

Though there is no particular limitation on the halogen atom, concrete examples of the halogen atom that can be favorably used in the present invention include fluorine atom, chlorine atom and bromine atom.

Though there is no particular limitation on the position of the substituent of the substituted or unsubstituted aryl group or on the number of the subsituents, it is desired that the aryl group is substituted at the meta-position and/or the para-position, and the total number of the substituents is generally not larger than 3 and, preferably, not larger than 2.

There is no particular limitation on the substituted or unsubstituted heteroaryl group provided it is a substituted or unsubstituted heteroaryl group including a hetero atom such as oxygen atom, nitrogen atom or sulfur atom. It is, however, desired to use a substituted or unsubstituted heteroaryl group having 4 to 12 carbon atoms. Preferred examples of the unsubstituted heteroaryl group include furyl group, benzofuryl group, pyryl group, thienyl group, benzothienyl group, oxazolyl group, imidazolyl group, and pyrazolyl group. From the standpoint of easy synthesis, however, it is desired to use the furyl group and the thienyl group. Preferred substituents of the substituted heteroaryl group will be the same as the preferred substitutes of the substituted aryl group. There is no particular limitation on the position of the substituent of the substituted heteroaryl group and on the number of the substituents. Preferably, however, the heteroaryl group is substituted at the third position and/or the fourth position, the total number of the substituents is generally not larger than 3 and, preferably, not larger than 2.

There is no particular limitation on the substituted or unsubstituted adamantane ring, substituted or unsubstituted bicyclononane ring or substituted or unsubstituted norbornane ring formed by the groups R2 and R3 that are coupled together. Preferably, however, there is used a 2-adamantane ring, a bicyclo[3,1,1]-9-nonane ring or a 2-norbornane ring. Preferred substituents of the substituted adamantane ring, substituted bicyclononane ring or substituted norbornane ring will be the same as the preferred substituents of the substituted aryl group. There is no particular limitation on the position of the substituent of the substituted adamantane ring, substituted bicyclononane ring or substituted norbornane ring or on the number of the substituents. From the standpoint of easy synthesis, however, it is desired to use the ring in an unsubstituted form.

The substituent R4 in the above-mentioned general formula (1) is the one at the seventh position, eighth position, ninth position or tenth position of the naphthopyrane ring. This substituent is usually introduced in order to adjust a maximum absorption wavelength that affects the tone of color developed by the chromene compound of the present invention. In the present invention, therefore, an optimum substituent is selected depending upon a desired tone of color.

Though there is no particular limitation on the substituent R4, there can be used the same substituents as those of the above-mentioned substituted or unsubstituted aryl group. Particularly preferred examples of the substituent R4 include alkyl group, aryl group, halogen atom, aralkyl group and alkoxyl group. As the alkyl group, there can be generally used the one having 1 to 4 carbon atoms though there is no particular limitation on the number of carbon atoms. Preferred examples Of the alkyl group include methyl group, ethyl group, propyl group and butyl group. Though there is no particular limitation on the number of carbon atoms of the aryl group, it is generally desired that the aryl group has 6 to 10 carbon atoms. Preferred examples of the aryl group include phenyl group and naphthyl group. As the halogen Atom, there can be used a fluorine atom, a chlorine atom, a bromine atom or an iodine atom. Though there is no particular limitation on the number of carbon atoms of the aralkyl group, it is generally desired to use an aralkyl group having 7 to 11 carbon atoms. Preferred examples of the aralkyl group include benzyl group, phenylethyl group, phenylpropyl group and phenylbutyl group. Though there is no particular limitation on the number of carbon atoms of the alkoxyl group, it is generally desired to use an alkoxyl group having 1 to 5 carbon atoms. Preferred examples of the alkoxyl group include methoxy group, ethoxyl group, n-propoxy group, isopropoxy group, n-butoxy group, sec-butoxy group and t-butoxy group.

In the general formula (1), n is the number of the substituents R4 and is an integer of 0 to 4. The value n may be from 0 to 4. For easy synthesis, however, n is preferably not larger than 3 and, more preferably, not larger than 2. When n is not smaller than 2, the substituents R4 may be the same ones or the different ones.

In the general formula (1), R5 is a hydrogen atom or a substituent. There is no particular limitation when R5 is a substituent. In this case, the substituent R5 is the same as the substituent R4. From the standpoint of suppressing color due to aging, however, it is desired that R5 is a hydrogen atom.

In the general formula (1), when R1 is an alkyl group in which a carbon atom bonded to the naphthopyrane ring is a primary carbon atom, R2 and R3 are groups represented by the following formula (2),

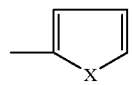

(2)

wherein X is an oxygen atom or a sulfur atom, or groups represented by the following formula (3),

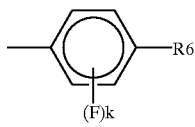

(3)

wherein R6 is an alkoxyl group or a trifluoromethoxy group, and k is 0 or 1, which may be different from each other, and at least either one of them is a group represented by the above formula (3), and R5 is a hydrogen atom.

The above formula (2) Represents a 2-thienyl group or a 2-furanyl group. From the standpoint of color density, the furanyl group is preferred since it develops color of a high density. From the standpoint of initial color (color of before being irradiated with light containing ultraviolet rays), on the other hand, the thienyl group is preferred since it initially develops less color.

In the above-mentioned formula (3), the substituent R6 is an alkoxyl group or a trifluoromethoxy group. As the alkoxyl group, it is desired to use an alkoxyl group having 1 to 5 carbon atoms and, particularly, an alkoxyl group having 1 to 2 carbon atoms from the standpoint of easy synthesis.

Preferred examples of the alkoxyl group used in the present invention include methoxy group and ethoxy group. As the substituent R6, an alkoxyl group is preferred since it enables the fading rate to be increased.

When the group represented by the above formula (3) has a fluorine atom as a substituent, it is desired that the fluorine atom is substituted at a position neighboring the substituent R6 (ortho position relative to R6) in order to decrease the initial color, though there is no particular limitation on the position at where the fluorine atom is substituted.

Preferred examples of the group of the formula (3) include 4-methoxyphenyl group, 4-methoxy-3-fluorophenyl group, 4-ethoxyphenyl group and 4-trifluorophenyl group. It is desired that the combination of R2 and R3 is represented by the above-mentioned formula (3) from the standpoint of durability in the photochromic property.

Among the chromene compounds of the present invention, it is desired to use chromene compounds represented by the following formulas since they can be synthesized maintaining a good yield and exhibit small changes in the color after the coloring-fading cycles are repeated,

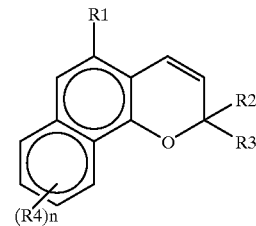

wherein
R1 is a methyl group or an ethyl group, R2 and R3 are thienyl groups or groups represented by the following formula (3),

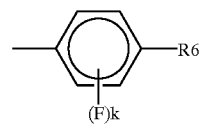

(3)

wherein R6 is an alkoxyl group or a trifluoromethoxy group, and k is 0 or 1, wherein R2 and R3 may be different from each other, but at least either R2 or R3 is a group represented by the above formula (3), and R4 and n are as defined in the above-mentioned formula (1),

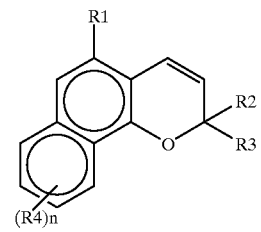

wherein R1 is an alkyl group having 3 to 15 carbon atoms and in which a carbon atom bonded to the naphthopyrane ring is a secondary carbon atom or a tertiary carbon atom, R2 and R3 are aryl groups having 6 to 14 carbon atoms which may be different from each other, R4 is a group selected from alkyl group, alkoxyl group, aryl group, acyloxyl group and hydroxyl group, n is an integer of 0 to 2 and when n is 2, R4 may be the same or different groups,

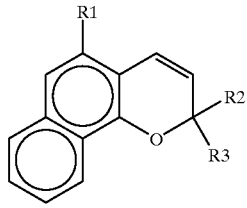

R1 is an alkyl group having 3 to 15 carbon atoms and in which a carbon atom bonded to the naphthopyrane ring is a secondary carbon atom or a tertiary carbon atom, and R2 and R3 are substituted or unsubstituted heteroaryl groups having 4 to 12 carbon atoms which may be different from each other,

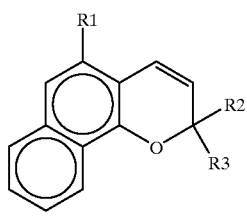

wherein R1 is an alkyl group having 3 to 15 carbon atoms and in which a carbon atom bonded to the naphthopyrane ring is a secondary carbon atom or a tertiary carbon atom, R2 is a substituted or unsubstituted heteroaryl group having 4 to 12 carbon atoms, and R3 is a substituted aryl group having 6 to 14 carbon atoms,

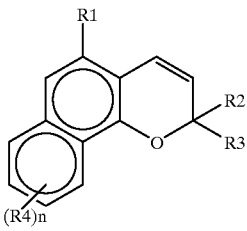

wherein R1 is an alkyl group having 3 to 15 carbon atoms and in which a carbon atom bonded to the naphthopyrane ring is a secondary carbon atom or a tertiary carbon atom, R2 and R3 form a substituted or unsubstituted norbornane ring having 7 to 13 carbon atoms by being coupled to each other, R4 is a group selected from alkyl group, alkoxyl group, aryl group, acyloxyl group and hydroxyl group, n is an integer of 0 to 2 and when n is 2, R4 may be the same or different groups,

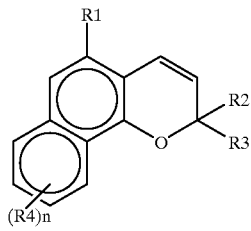

wherein R1 is an alkyl group having 3 to 15 carbon atoms and in which a carbon atom bonded to the naphthopyrane ring is a secondary carbon atom or a tertiary carbon atom, R2 and R3 form a substituted or unsubstituted bicyclononane ring having 9 to 15 carbon atoms by being coupled to each other, R4 is a group selected from alkyl group, alkoxyl group, aryl group, acyloxyl group and hydroxyl group, n is an integer of 0 to 2 and when n is 2, R4 may be the same or different groups, and

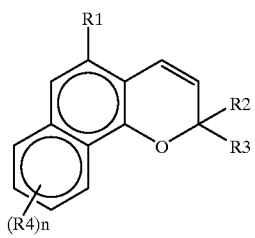

wherein R1 is an alkyl group having 3 to 15 carbon atoms and in which a carbon atom bonded to the naphthopyrane ring is a secondary carbon atom or a tertiary carbon atom, R2 and R3 form a substituted or unsubstituted adamantane ring having 10 to 16 carbon atoms by being coupled to each other, R4 is a group selected from alkyl group, alkoxyl group, aryl group, acyloxyl group and hydroxyl group, n is an integer of 0 to 2 and when n is 2, R4 may be the same or different groups.

Furthermore, there can be used the chromene compounds represented by the following formulas since they can be synthesized maintaining a good yield, exhibit a small change in the developed color after the coloring-fading cycles and exhibit large fading rates,

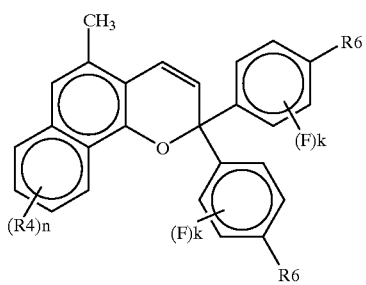

wherein R4, R6, k and n are as defined in the above-mentioned formulas (1) and (3),

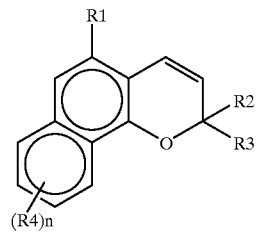

wherein R1 is an isopropyl group or a t-butyl group, R2 and R3 are substituted aryl groups having 6 to 14 carbon atoms which may be different from each other, R4 is a group selected from alkyl group, alkoxyl group, aryl group, acyloxyl group and hydroxyl group, and n is an integer of 0 to 2 and when n is 2, R4 may be the same or different groups,

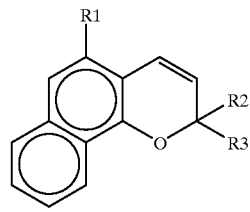

wherein R1 is an isopropyl group or a t-butyl group, and R2 and R3 are substituted or unsubstituted heteroaryl groups having 4 to 12 carbon atoms which may be different from each other,

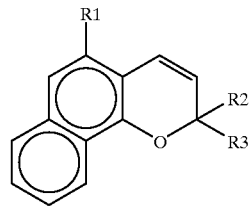

wherein R1 is an isopropyl group or a t-butyl group, R2 is a substituted or unsubstituted heteroaryl group having 4 to 12 carbon atoms, and R3 is a substituted aryl group having 6 to 14 carbon atoms,

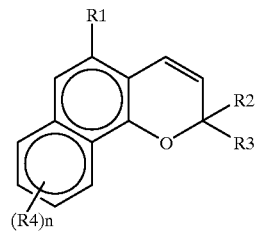

wherein R1 is an isopropyl group or a t-butyl group, R2 and R3 form a substituted or unsubstituted norbornane ring having 7 to 13 carbon atoms by being coupled to each other, R4 is a group selected from alkyl group, alkoxyl group, aryl group, acyloxyl group and hydroxyl group, and n is an integer of 0 to 2 and when n is 2, R4 may be the same or different groups,

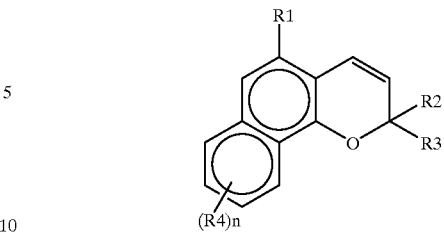

wherein R1 is an isopropyl group or a t-butyl group, R2 and R3 form a substituted or unsubstituted bicyclononane ring having 9 to 15 carbon atoms by being coupled to each other, R4 is a group selected from alkyl group, alkoxyl group, aryl group, acyloxyl group and hydroxyl group, and n is an integer of 0 to 2 and when n is 2, R4 may be the same or different groups, and

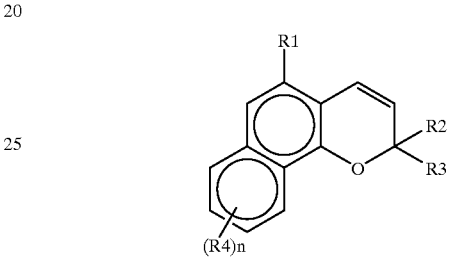

wherein R1 is an isopropyl group or a t-butyl group, R2 and R3 form a substituted or unsubstituted adamantane ring having 10 to 16 carbon atoms by being coupled to each other, R4 is a group selected from alkyl group, alkoxyl group, aryl group, acyloxyl group and hydroxyl group, and n is an integer of 0 to 2 and when n is 2, R4 may be the same or different groups.

Concrete examples of the chromene compound that can be favorably used in the present invention include:
1) 5-methyl-2,2-bis(4-methoxyphenyl)-2H-benzo(h) chromene;
2) 5-methyl-2,2-bis(3-fluoro-4-methoxyphenyl)-2H-benzo(h) chromene;
3) 5-ethyl-2,2-bis(4-methoxyphenyl)-2H-benzo(h) chromene;
4) 5-methyl-2,2-bis(4-methoxyphenyl)-2H-benzo(h) chromene;
5) 5-methyl-2-(4-methoxyphenyl)-2-(4-trifluoromethoxyphenyl)-2H-benzo(h) chromene;
6) 5-methyl-2-(2-furyl)-2-(3-fluoro-4-methoxyphenyl)-2H-benzo(h) chromene;
7) 5-methyl-2-(2-thienyl)-2-(4-methoxyphenyl)-2H-benzo(h) chromene;
8) 7-methoxy-5-methyl-2,2-bis(4-methoxyphenyl)-2H-benzo(h) chromene;
9) 5-methyl-2-(4-methoxyphenyl)-2-(3-fluoro-4-methoxyphenyl)-2H-benzo(h) chromene;
10) 5-n-propyl-2,2-bis(4-methoxyphenyl)-2H-benzo(h) chromene;
11) 5-tert-butyl-2,2-diphenyl-2H-benzo(h) chromene;
12) 5-tert-butyl-2-bicyclo[3.3.1]nonane-2H-benzo(h) chromene;
13) 5-tert-pentyl-2-(2-furyl)-2-(4-methoxyphenyl)-2H-benzo(h) chromene
14) 5-sec-butyl-2-(3-cyano-4-methoxyphenyl)-2-(4-methoxyphenyl)-2H-benzo(h) chromene;
15) 5-(1-ethyl-1-methylpropyl)-2,2-bis(3-fluoro-4-methoxyphenyl)-2H-benzo h) chromene;

16) 5-t-butyl-2-phenyl-2-(2-thienyl)-2H-benzo(h) chromene;
17) 5-isopropyl-2-(2-naphthyl)-2-(phenyl)-2H-benzo(h) chromene;
18) 8-methoxy-2-(2-N-methylpyryl)-2-phenyl-5-(2-phenyl-1-methyl ethyl)-2H-benzo(h) chromene;
19) 8-hydroxy-5-isopropyl-2,2-bis(2-thienyl)-2H-benzo(h) chromene;
20) 8-acetoxy-5-isopropyl-2,2-bis(4-methylphenyl)-2H-benzo(h) chromene;
21) 5-isopropyl-2,2-diphenyl-2H-benzo(h) chromene;
22) 5-isopropyl-2,2-bis(3-fluoro)-4-methoxyphenyl)-2H-benzo(h) chromene;
23) 5-isopropyl-2-(4-methoxyphenyl)-2-(4-trifluoromethoxyphenyl)-2H-benzo(h) chromene;
24) 5-isopropyl-2-phenyl-2-(4-trifluoromethoxyphenyl)-2H-benzo(h) chromene; and
25) 5-isopropyl-2,2-bis(4-methoxyphenyl)-2H-benzo(h) chromene.

The chromene compound represented by the above-mentioned general formula (1) of the present invention usually exists in the form of a colorless or pale yellow solid or a viscous liquid at normal temperature under normal pressure, and can be confirmed by means (a) to (c) described below.
(a) Measurement of the proton nucleus magnetic resonance spectrum ($^1$H-NMR) indicates peaks near δ5.5 to 9.0 ppm due to an aromatic proton and a proton of an alkene, and peaks near δ1.0 to 4.0 ppm due to protons of an alkyl group and an alkylene group. Upon relatively comparing the spectral intensities, furthermore, it is possible to know the number of protons of the bonded groups.
(b) The composition of a corresponding product can be determined based on the elemental analysis.
(c) Measurement of the $^{13}$C-nuclear magnetic resonance spectrum ($^{13}$C-NMR) indicates a peak near δ110 to 160 ppm based on a carbon atom of an aromatic hydrocarbon group, a peak near δ80 to 140 ppm due to a carbon atom of an alkene, and peaks near δ20 to 80 ppm due to carbon atoms of an alkyl group and an alkylene group.

The chromene compound represented by the above-mentioned general formula (1) of the present invention can be synthesized by any method without any particular limitation. A representative method that is generally preferably employed will be described below.

A compound of the present invention represented by the general formula (1) wherein R1 is an alkyl group in which a carbon atom bonded to the naphthopyane ring is a primary carbon atom can be produced by, for example, the following process A.

Process A

A naphthol derivative represented by the following general formula (4),

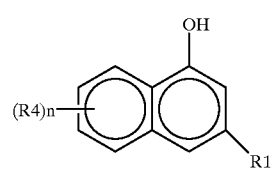

(4)

wherein R1 is an alkyl group in which a carbon atom bonded to the naphthopyrane ring is a primary carbon atom, and R4 and n are as defined in the general formula (1), is reacted with a propargyl alcohol derivative represented by the following general formula (5),

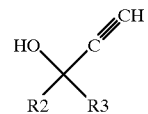

(5)

wherein R2 and R3 are as defined in the general formula (1), in the presence of an acid catalyst.

There is no particular limitation on the methods of synthesizing the compounds represented by the above-mentioned general formulas (4) and (5). The naphthol derivative represented by the above-mentioned general formula (4) can be synthesized by, for example, reacting an o-bromoacetophenone and a propyne derivative at 10 to 160° C. for 10 minutes to 2 hours, and adding a potassium hexamethyldisilazide (KHMDS) at −78° C., followed by heating at 75° C. for 30 minutes to 2 hours. In this case, when an o-bromoacetophenone is used having substituents at the second position, third position, fourth position and fifth position, there can be synthesized a chromene compound having substituents at the tenth position, ninth position, eighth position and seventh position of the naphthopyrane ring.

Furthermore, the propargyl alcohol derivative represented by the above-mentioned general formula (5) can be synthesized by, for example, reacting a ketone derivative corresponding to the above-mentioned general formula (5) with a metal acetylene compound such as lithium acetylide.

The reaction of the compound represented by the above-mentioned general formula (4) with the compound represented by the above-mentioned general formula (5) is usually carried out as described below. That is, the reaction ratio of these two kinds of compounds is selected from a wide range, but is generally selected from a range of 1:10 to 10:1 (molar ratio). As the acid catalyst, furthermore, there is used sulfuric acid, benzenesulfonic acid, p-toluenesulfonic acid or acidic alumina in an amount of from 0.1 to 10 parts by weight with respect to the sum of 100 parts by weight the reaction substrates represented by the above-mentioned general formulas (4) and (5). The reaction temperature is, usually, from 0 to 200° C. As the solvent, there is used a non-protonic organic solvent such as N-methylpyrrolidone, dimethylformamide, tetrahydrofuran, benzene or toluene.

A compound of the present invention represented by the general formula (1) wherein R1 is an alkyl group in which a carbon atom bonded to the naphthopyane ring is a secondary carbon atom or a tertiary carbon atom, and R2 and R3 are aryl groups or heteroaryl groups, can be produced by, for example, the following process B.

Process B

A naphthol derivative represented by the following general formula (4'),

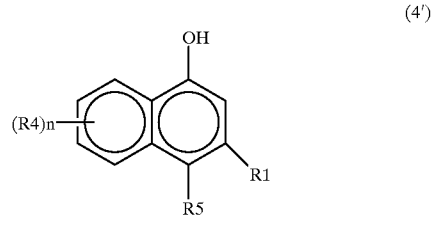

(4')

wherein R1 is an alkyl group in which a carbon atom bonded to the naphthopyrane ring is a secondary carbon atom or a tertiary carbon atom, and R4, R5 and n are as defined in the general formula (1), is reacted with a propargyl alcohol represented by the following general formula (5),

(5)

wherein R2 and R3 are as defined in the general formula (1), in the presence of an acid catalyst.

There is no particular limitation on the methods of synthesizing the compounds represented by the above-mentioned general formulas (4') and (5). The naphthol derivative represented by the above-mentioned general formula (4') can be synthesized by, for example, reacting a phenylacetyl chloride and an acetylene derivative at 180° C. followed by hydrolysis. In this case, when a phenylacetyl chloride is used having substituents at the second position, third position, fourth position and fifth position, there can be synthesized a chromene compound having substituents at the tenth position, ninth position, eighth position and seventh position of the naphthopyrane ring.

Furthermore, the propargyl alcohol derivative represented by the above-mentioned general formula (5) can be synthesized by, for example, reacting a ketone derivative corresponding to the above-mentioned general formula (5) with a metal acetylene compound such as lithium acetylide.

The reaction of the compound represented by the above-mentioned general formula (4') with the compound represented by the above-mentioned general formula (5) is usually carried out as described below. That is, the reaction ratio of these two kinds of compounds is selected from a wide range, but is generally selected from a range of 1:10 to 10:1 (molar ratio). As the acid catalyst, furthermore, there is used sulfuric acid, benzenesulfonic acid, p-toluenesulfonic acid or acidic alumina in an amount of from 0.1 to 10 parts by weight with respect to the sum of the reaction substrates represented by the above-mentioned general formulas (4') and (5). The reaction temperature is, usually, from 0 to 200° C. As the solvent, there is used a non-protonic organic solvent such as N-methylpyrrolidone, dimethylformamide, tetrahydrofuran, benzene or toluene.

A compound of the present invention represented by the general formula (1) wherein R2 and R3 are coupled to each other to form an adamantane ring, a bicyclononane ring or a norbornane ring, can be produced by, for example, the following process C.

Process C

A naphthol derivative represented by the following general formula (4'),

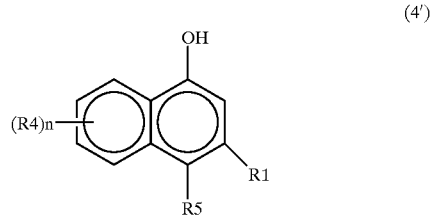

(4')

wherein R1, R4, R5 and n are as defined in the general formula (1), is reacted with an aldehyde derivative represented by the following general formula (6),

(6)

wherein R2 and R3 form an adamantane ring, a bicyclononane ring or a norbornane ring as defined in the general formula (1), in the presence of a metal alkoxide.

There is no particular limitation on the method of synthesizing the compound represented by the above-mentioned general formula (6). That is, the aldehyde derivative represented by the above-mentioned general formula (6) can be synthesized by, for example, reacting a Schiff base obtained from an acetaldehyde and a cyclohexylamine with a lithium diisopropylamide, followed by the reaction with a ketone derivative having a substituent corresponding to the above general formula (6).

Thereafter, the reaction is carried out in an aqueous solution of an oxalic acid.

The reaction of the compound represented by the above-mentioned general formula (4') with the compound represented by the above-mentioned general formula (6) is usually carried out as described below. That is, the reaction ratio of these two kinds of compounds is selected from a wide range, but is generally selected from a range of 1:10 to 10:1 (molar ratio). As the metal alkoxide, furthermore, there is used a tetraethoxytitanic acid or the like acid in an amount of from 0.25 to 10 parts by weight with respect to the compound represented by the above-mentioned general formula (4'). The reaction temperature is, usually, from 0 to 200° C. As the solvent, there is used a non-protonic organic solvent such as N-methylpyrrolidone, dimethylformamide, tetrahydrofuran, benzene or toluene.

The chromene compound of the present invention represented by the above-mentioned general formula (1) dissolves well in a general organic solvent such as toluene, chloroform or tetrahydrofurane. When the chromene compound of the present invention represented by the above-mentioned general formula (1) is dissolved in such a solvent, the solution is generally nearly colorless and transparent. When irradiated with sunlight or ultraviolet rays, however, the solution readily develops color and returns back to its initial colorless state when light is shut off; i.e., the solution exhibits a favorable and reversible photochromic action. The photochromic fluid can be used for such applications as ornamental uses.

The chromene compounds of the present invention represented by the general formula (1) can be used in a single kind or being mixed together in two or more kinds depending upon the purpose of use. Furthermore, the chromene compounds of the present invention can be combined together with other chromene compounds to obtain a chromene composition exhibiting more excellent photochromic properties.

As the other chromene compound to be used in combination, there can be favorably used a chromene compound represented by the following general formula (7),

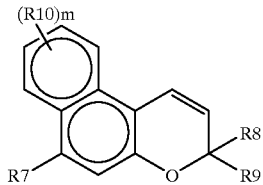

(7)

wherein R7 is AN AMINO GROUP represented by the following formula (8),

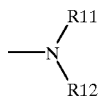

(8)

wherein R11 and R12 are hydrogen atoms, substituted or unsubstituted alkyl groups having 1 to 10 carbon atoms, or substituted or unsubstituted aromatic hydrocarbon groups or heterocyclic groups having 6 to 10 carbon atoms, which may be different from each other, or a substituted or unsubstituted heterocyclic group having a nitrogen atom as a hetero atom and in which the nitrogen atom is bonded to the naphthopyrane ring, or a condensed heterocyclic group formed by the condensation of the above heterocyclic group with an aromatic hydrocarbon ring or an aromatic heterocyclic ring, R8 and R9 are substituted or unsubstituted aromatic hydrocarbon groups, substituted or unsubstituted aromatic heterocyclic groups or alkyl groups, which may be different from each other, R10 is a substituent, and m is an integer of 0 to 4 representing the number of the substituents R10 and when m is not smaller than 2, R10 may be the same or different groups.

When the chromene compound represented by the general formula (7) is used alone, a high color-developing sensitivity is obtained and a high fading rate is obtained accompanied, however, by a large initial color and a large degree of coloring after aged. By mixing the chromene compound of the general formula (7) to the chromene compound represented by the general formula (1), however, the initial color can be decreased and color due to aging can be decreased, too, though the color-developing sensitivity decreases to some extent.

In the above-mentioned general formula (7), R7 is an amino group represented by the above formula (8) or a substituted or unsubstituted heterocyclic group having a nitrogen atom as a hetero atom and in which the nitrogen atom is bonded to the naphthopyrane ring, or a condensed heterocyclic ring formed by the condensation of the above heterocyclic group with an aromatic hydrocarbon ring or an aromatic heterocyclic ring.

As the substituted or unsubstituted alkyl group having 1 to 10 carbon atoms or as the substituted or unsubstituted aromatic hydrocarbon group or heterocyclic group having 6 to 10 carbon atoms represented by R11 and R12 in the above-mentioned formula (8), there can be used any known group without any particular limitation. As the alkyl group, aromatic hydrocarbon group or heterocyclic group, there can be used an alkyl group having 1 to 4 carbon atoms, a benzene ring or a naphthalene ring, As the substituent for the alkyl group, aromatic hydrocarbon group or heterocyclic group, furthermore, there can be used a hydroxyl group, a cyano group or a halogen atom.

Concrete examples of the amino group represented by the above formula (8) include methylamino group, ethylamino group, propylamino group, isopropylamino group, dimethylamino group, diethylamino group, dipropylamino group, methylethylamino group, 2-hydroxyethylamino group, di(hydroxyethyl)amino group, di(cyanomethyl)amino group and diphenylamino group. The substituents R11 and R12 may be the same or different.

Referring to the substituted or unsubstituted heterocyclic group having a nitrogen atom as a hetero atom and in which the nitrogen atom is bonded to the naphthopyrane ring or the condensed heterocyclic group formed by the condensation of the above heterocyclic group with an aromatic hydrocarbon ring or an aromatic heterocyclic ring, represented by R7 in the general formula (7), it is desired that the number of carbon atoms constituting the heterocyclic group is from 2 to 10 and, more preferably, from 2 to 6. The ring may contain a hetero atom in addition to the nitrogen atom bonded to the naphthopyrane ring. Though there is no limitation, it is desired that the hetero atom is an oxygen atom, a sulfur atom or a nitrogen atom. AS the aromatic hydrocarbon ring or the aromatic heterocyclic ring to be condensed with the heterocyclic group, there can be used an aromatic hydrocarbon ring or an aromatic heterocyclic ring having 6 to 10 carbon atoms, which will be a benzene ring, a thiophene ring or a furan ring. As the substituted or unsubstituted heterocyclic ring having the nitrogen atom as a hetero atom and which is bonded to the naphthopyrane ring through the nitrogen atom, or as the condensed heterocyclic group formed by the condensation of the above heterocyclic group with an aromatic hydrocarbon ring or an aromatic heterocyclic ring, there can be exemplified pyrrolidinyl group, piperidino group, hexamethyleneimino group, 2,2,6,6-tetramethylpiperidino group, morpholino group, 2,6-dimethylmorpholino group, N-methylpiperadinyl group, thiomorpholino group, indolyl group, methylindolyl group, tetrahydroquinolyl group and aziridinyl group.

In the above-mentioned general formula (7), R8 and R9 are substituted or unsubstituted aromatic hydrocarbon groups, substituted or unsubstituted aromatic heterocyclic groups or alkyl groups, which may be different from each other.

Though there is no particular limitation on the aromatic hydrocarbon group, it is generally desired to use an aromatic hydrocarbon group having 6 to 10 carbon atoms. Concrete examples of the aromatic hydrocarbon group include phenyl group, 2-naphthyl group and 1-naphthyl group.

Though there is no particular limitation on the aromatic heterocyclic group, it is generally desired to use an aromatic heterocyclic group having 3 to 20 carbon atoms and, preferably, 3 to 12 carbon atoms. There is no particular limitation on the hetero atom contained in the aromatic heterocyclic group. Preferably, however, the hetero atom is an oxygen atom, a sulfur atom or a nitrogen atom, and its number is from 1 to 3 and, preferably from 1 to 2. When hetero atoms are contained in a plural number in the aromatic heterocyclic group, those hetero atoms may be of the same kind or of different kinds. Moreover, the aromatic heterocyclic group may be ring-condensed with an aromatic ring. As the aromatic ring which may be ring-condensed, there can be used an aromatic ring having 6 to 10 carbon atoms, such as benzene ring or naphthalene ring. Concrete examples of the aromatic heterocyclic group include furyl group, thienyl group, pyrrolyl group, benzofuryl group, indole group, quinolyl group, isoquinolyl group, dibenzofuryl group and carbazole group.

Though there is no particular limitation, the alkyl group generally has 1 to 5 carbon atoms and, preferably, 1 to 3 carbon atoms. Concrete examples of the alkyl group include methyl group, ethyl group, n-propyl group and isopropyl group. By taking the practicable durability into consideration, the methyl group is most preferred.

The aromatic hydrocarbon group and aromatic heterocyclic group represented by R8 and R9 may have any known substituent, and there is no limitation on the kind thereof. Preferably, however, there can be used alkyl group, alkoxyl group, alkoxyalkoxyl group, aryloxyl group, alkoxyalkyl group, aralkyl group, substituted amino group, substituted or unsubstituted heterocyclic group having a nitrogen atom as a hetero atom and in which the nitrogen atom is bonded to the aromatic hydrocarbon group and to the aromatic heterocyclic group, acyloxyl group, hydroxyl group, acyl group, alkoxycarbonyl group, aryloxycarbonyl group, halogen atom, cyano group, trifluoromethyl group, trifluoromethoxy group and nitro group. There is no particular limitation on the positions and the numbers of the substituents bonded to the aromatic hydrocarbon group and to the aromatic heterocyclic group. Preferably, however, the number of the substituents is 0 to 4 and, preferably, 0 to 3. These substituents may be of the same kind or may be of different kinds and may be used in combination without any limitation.

There is no particular limitation on the alkyl group which is a substituent for the aromatic hydrocarbon group or the aromatic heterocyclic group represented by R8 and R9. Generally, however, the alkyl group has 1 to 10 carbon atoms and, preferably, 1 to 4 carbon atoms. Concrete examples of the alkyl group include methyl group, ethyl group, n-propyl group, isopropyl group, n-butyl group and t-butyl group.

Though there is no particular limitation, the alkoxyl group generally has 1 to 10 carbon atoms and, preferably, 1 to 4 carbon atoms. Concrete examples of the alkoxyl group include methoxy group, ethoxyl group, n-propoxyl group, isopropoxyl group, n-butoxy group and t-butoxy group.

Though there is no particular limitation, the alkoxyalkoxyl group generally has 2 to 20 carbon atoms and, preferably, 3 to 10 carbon atoms. Concrete examples of the alkoxyalkoxyl group include methoxyethoxyl group, ethoxyethoxyl group, methoxypropoxyl group and methoxybutoxy group.

Though there is no particular limitation, the aryloxyl group generally has 6 to 14 carbon atoms and, preferably, 6 to 10 carbon atoms. Concrete examples of the aryloxyl group include phenoxy group, 1-naphthoxy group and 2-naphthoxy group.

Though there is no particular limitation, the alkoxyalkyl group generally has 2 to 10 carbon atoms and, preferably, 2 to 6 carbon atoms. Concrete examples of the alkoxyalkyl group include methoxymethyl group, ethoxymethyl group, propoxymethyl group, dimethoxymethyl group, 2,2-dioxacyclopentane-1-il group and butoxymethyl group.

Though there is no particular limitation, the aralkyl group generally has 7 to 16 carbon atoms and, preferably, 7 to 10 carbon atoms. Concrete examples of the aralkyl group include benzyl group, phenylethyl group, phenylpropyl group and phenylbutyl group.

Though there is no particular limitation, the acyloxyl group generally has 1 to 15 carbon atoms and, preferably, 1 to 6 carbon atoms. Concrete examples of the acyloxyl group include acetoxyl group, propionyloxy group, butyryloxy group, (meth)acryloyloxy group and benzoyloxy group.

Though there is no particular limitation, the substituted amino group generally has a substituent such as an alkyl group with 1 to 10 carbon atoms, or a hydroxy-substituted alkyl group. Concrete examples of the substituted amino group include methylamino group, ethylamino group, propylamino group, isopropylamino group, dimethylamino group, diethylamino group, dipropylamino group, methylethylamino group, 2-hydroxyethylamino group and di(hydroxyethyl)amino group.

Referring to the substituted or unsubstituted heterocyclic group having a nitrogen atom as a hetero atom and in which the nitrogen atom is bonded to the aromatic hydrocarbon group and to the aromatic heterocyclic group, it is desired that the number of carbon atoms constituting the heterocyclic group is from 2 to 10 and, preferably, from 2 to 6. The ring may contain a hetero atom in addition to the nitrogen atom bonded to the aromatic hydrocarbon group and to the aromatic heterocyclic group. Though there is no particular limitation, it is desired that the hetero atom is an oxygen atom, a sulfur atom or a nitrogen atom. As the substituted or unsubstituted heterocyclic group having the nitrogen atom as a hetero atom and in which the nitrogen atom is bonded to the aromatic hydrocarbon group and to the aromatic heterocyclic group, there can be exemplified pyrrolidinyl group, piperidino group, hexamethyleneimino group, 2,2,6,6-tetramethylpiperidino group, morpholino group, 2,6-dimethylmorpholino group, N-methylpiperadinyl group and thiomorpholino group.

Though there is no particular limitation, the alkoxycarbonyl group generally has 1 to 10 carbon atoms and, preferably, 1 to 7 carbon atoms. Concrete examples of the alkoxycarbonyl group include methoxycarbonyl group, ethoxycarbonyl group, (iso)propoxycarbonyl group, and (iso, t-)butyloxycarbonyl group.

Though there is no particular limitation on the aryloxycarbonyl group, the aryl group is an aryloxy group having generally 6 to 14 carbon atoms and, preferably, 6 to 10 carbon atoms. Concrete examples of the aryloxycarbonyl group include phenoxycarbonyl group, 1-naphthoxycarbonyl group and 2-naphthoxycarbonyl group.

Though there is no particular limitation, the acyl group generally has 1 to 15 carbon atoms and, preferably, 1 to 7 carbon atoms. Concrete examples of the acyl group include formyl group, acetyl group, propionyl group, butylyl group and benzoyl group.

Though there is no particular limitation, the halogen atom is generally a fluorine atom, a chlorine atom, a bromine atom or an iodine atom.

In the above-mentioned general formula (7), R10 is a substituent substituted for the seventh position, eighth position, ninth position and tenth position of the naphthopyrane ring. Introduction of the substituent does not seriously affect the effect of the present invention. As the substituent, there can be used alkyl group, alkoxyl group, aralkyl group, acyl group, alkoxycarbonyl group, substituted amino group, substituted or unsubstituted heterocyclic group having a nitrogen atom as hetero atom and in which the nitrogen atom is bonded to the naphthopyrane ring, aromatic hydrocarbon group, acyloxyl group, nitro group, hydroxyl group or halogen atom. As the aromatic hydrocarbon group, though there is no particular limitation on the number of carbon atoms, it is desired to use an aromatic hydrocarbon group having 6 to 14 carbon atoms. Preferred examples of the aromatic hydrocarbon group include phenyl group, tolyl group, xylyl group and naphthyl group. Other substituents may be those groups or atoms described above concerning the substituents that may be possessed by the substituted or unsubstituted aromatic hydrocarbon group and aromatic heterocyclic group represented by R8 and R9.

In the general formula (7), m is a number of the substituents R10 and is an integer of 0 to 4. The value m may be from 0 to 4. From the standpoint of synthesis, however, it is desired that m is not larger than 3 and, preferably, not larger than 2. When m is not smaller than 2, R10 may be the same or different groups.

As the chromene compound represented by the general formula (7), there can be preferably used a chromene compound represented by the following formula since it exhibits a practically sufficient color-developing sensitivity and a large fading rate,

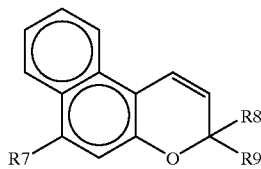

wherein R7 is a substituted amino group represented by the following formula (8),

(8)

wherein R11 and R12 are substituted or unsubstituted alkyl groups having 1 to 10 carbon atoms, which may be different from each other, or a substituted or unsubstituted pyrrolydinyl group, morpholino group, piperidino group, thiomorpholino group, aziridinyl group, piperadinyl group, hexamethyleneimino group, indolyl group or tetrahydroquinolyl group, R8 and R9 are substituted or unsubstituted phenyl groups, naphthyl groups, furyl groups, thienyl groups, pyrrolyl groups, benzofuryl groups, benzothienyl groups or methyl groups, which may be different from each other.

In the chromene composition of the present invention, concrete and preferred examples of the chromene compound represented by the general formula (7) include:
1) 6-morpholino-3,3-bis(3-fluoro-4-methoxyphenyl)-3H-benzo(f) chromene;
2) 6-morpholino-3-(4-methoxyphenyl)-3-(4-trifluoromethoxyphenyl)-3H-benzo(f) chromene;
3) 6-piperidino-3-methyl-3-(2-naphthyl)-3H-benzo(f) chromene;
4) 6-piperidino-3-methyl-3-phenyl-3H-benzo(f) chromene;
5) 6-morpholino-3,3-bis(4-methoxyphenyl)-3H-benzo(f) chromene;
6) 6-hexamethyleneimino-3-methyl-3-(4-methoxyphenyl)-3H-benzo(f) chromene;
7) 6-morpholino-3-(2-furyl)-3-methyl-3H-benzo(f) chromene;
8) 6-morpholino-3-(2-thienyl)-3-methyl-3H-benzo(f) chromene; and
9) 6-morpholino-3-(2-benzofuryl)-3-methyl-3H-benzo(f) chromene.

The chromene compounds represented by the general formula (7) can be used in a single kind or being mixed in two or more kinds depending upon the use.

In the chromene composition of the present invention, the chromene compound represented by the general formula (7) is blended in an amount of 10 to 1000 parts by weight, preferably, in an amount of 17 to 1000 parts by weight and, more preferably, in an amount of 17 to 500 parts by weight per 100 parts by weight of the chromene compound represented by the general formula (1). When the amount of the chromene compound represented by the general formula (7) exceeds 1000 parts by weight, the concentration of the chromene compound represented by the general formula (7) increases if it is attempted to obtain a sufficient degree of color density with the composition of the present invention, resulting in an increase in the initial color and an increase in the color after aged. When the amount of the chromene compound represented by the general formula is smaller than 10 parts by weight, the composition of the present invention exhibits a small degree of initial color, but tends to be insufficient in color density and color-developing sensitivity.

Color after aged can be improved if an ultraviolet ray-absorbing agent is added to the chromene composition of the present invention. A known ultraviolet ray-absorbing agent can be used without any limitation. A benzotriazole-type ultraviolet ray-absorbing agent or a benzophenone-type ultraviolet-ray absorbing agent is particularly preferred. As the benzotriazole-type ultraviolet ray-absorbing agent, there can be used a known compound having a benzotriazole skeleton and ultraviolet ray-absorbing ability without any limitation.

As the benzophenone-type ultraviolet ray absorbing agent, there can be used a known compound having a benzophenone skeleton and ultraviolet ray-absorbing ability without any limitation. There can be favorably used, for example, the following benzotriazole-type ultraviolet ray-absorbing agent and the benzophenone-type ultraviolet ray-absorbing agent.

*Benzotriazole-type Ultraviolet Ray-absorbing Agents (1) 2-(5-methyl-2-hydroxyphenyl)benzotriazole (trade name: Tinubin P, manufactured by Nippon Chiba Geigy Co.),
(2) 2-[2-hydroxy-3,5-bis(α,α-dimethylbenzyl)phenyl]-2H-benzotriazole (trade name; Tinubin 234, manufactured by Nippon Chiba Geigy Co.),
(3) 2-(3,5-di-t-butyl-2-hydroxyphenyl)benzotriazole (trade name: Tinubin 320, manufactured by Nippon Chiba Geigy Co.),
(4) 2-(3-t-butyl-5-methyl-2-hydroxyphenyl)-5-chlorobenzotriazole (trade name: Tinubin 326, manufactured by Nippon Chiba Geigy Co.),
(5) 2-(3,5-di-t-butyl-2-hydroxyphenyl)-5-chlorobenzotriazole (trade name: Tinubin 327, manufactured by Nippon Chiba Geigy Co.),
(6) 2-(3,5-di-t-amyl-2-hydroxyphenyl)benzotriazole (trade name: Tinubin 328, manufactured by Nippon Chiba Geigy Co.),
(7) 2-(2'-hydroxy-5'-t-octylphenyl)benzotriazole (trade name: Tinubin 329, manufactured by Nippon Chiba Geigy Co.).

*Benzophenone-type Ultraviolet Ray-absorbing Agents (1) 2-hydroxy-4-methoxybenzophenone (trade name: Sumisorb 110, manufactured by Sumitomo Kagaku Co.),
(2) 2-hydroxy-4-octyloxybenzophenone (trade name: Sumisorb 130, manufactured by Sumitomo Kagaku Co.), (3) bis(2-hydroxy-4-methoxy)benzophenone (trade name: Ubinal D-49, manufactured by BASF Co.),
(4) 2-hydroxybenzophenone (trade name: Ubinal 400, manufactured by BASF Co.),
(5) bis(2,4-dihydroxy)benzophenone (trade name: Ubinal D50, manufactured by BASF Co.),
(6) 2,4-dihydroxybenzophenone (trade name: Chemisorb 10, manufactured by Chemipro Kasei Co.),
(7) 2-hydroxy-4-dodecyloxybenzophenone (trade name: Chemisorb 13, manufactured by Chemipro Kasei Co.),
(8) 4-benzyloxy-2-hydroxybenzophenone (trade name: Chemisorb 15, manufactured by Chemipro Kasei Co.), and
(9) 2,2'-dihydroxy-4-methoxybenzophenone (trade name: Chemisorb 111, manufactured by Chemipro Kasei Co.).

It is desired that the above-mentioned ultraviolet ray-absorbing agents are blended in an amount of 1 to 500 parts by weight and, more preferably, 10 to 300 parts by weight per a total of 100 parts by weight of the chromene compound represented by the general formula (1) and the chromene compound represented by the general formula (7) from the standpoint of suppressing coloring after aging and preventing a drop in the color density of the chromene composition.

The chromene composition of the present invention comprising the chromene compound represented by the general formula (1) and the chromene compound represented by the general formula (7), exhibits a high color-developing sensitivity and a color tone which is yellowish to reddish. It is, however, also allowable to combine it with other photochromic compounds to obtain a photochromic composition which develops an intermediate color such as grey, amber or brown, which is generally preferred as a photochromic lens. Other photochromic compounds to be combined will preferably be a spirooxazine compound and a fulgimide compound.

As the spirooxazine compound, there can be used a known compound having a spirooxazine skeleton and photochromic property without any limitation. There can be preferably used, for example, a spirooxazine compound represented by the following general formula (9),

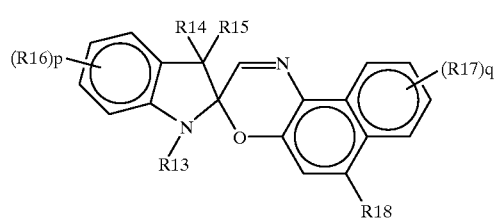

(9)

wherein R13 is an alkyl group which may be branched, R14 and R15 are alkyl groups which may be different from each other, and R14 and R15 may be coupled to each other to form a cycloalkane ring, R16 and R17 are alkyl groups, alkoxyl groups or halogen atoms, R18 is a hydrogen atom, or a substituted or unsubstituted heterocyclic group having a nitrogen atom as a hetero atom and in which the nitrogen atom is bonded to the naphthoxazine ring, or a condensed heterocyclic group formed by the condensation of the heterocyclic group with an aromatic hydrocarbon ring or an aromatic heterocyclic ring, p is an integer of 0 to 2 representing the number of the substituents R16, and q is an integer of 0 to 2 representing the number of the substituents R17.

As the alkyl groups represented by R13, R14 and R15 in the general formula (9), there can be used those alkyl groups having 1 to 5 carbon atoms, such as methyl group, ethyl group, isopropyl group, n-propyl group, n-butyl group, isobutyl group, and neopentyl group. As the cycloalkane ring formed by the groups A14 and R15 that are coupled together, there can be used a cyclopropane ring, a cyclobutane ring, a cyclopentane ring, a cyclohexane ring and a cycloheptane ring.

As the alkyl groups represented by R16 and R17 in the above-mentioned general formula (9), there can be used those alkyl groups having 1 to 5 carbon atoms, such as methyl group, ethyl group, isopropyl group, n-propyl group, n-butyl group, isobutyl group and neopentyl group.

As the alkoxyl groups represented by R16 and R17 in the above-mentioned general formula (9), there can be used those alkoxyl groups having 1 to 4 carbon atoms, such as methoxy, ethoxy, n-propoxyl group, n-butoxy group, isobutoxy group and t-butoxy group.

As the halogen atoms represented by R16 and R17 in the general formula (9), there can be used fluorine atoms, chlorine atoms and bromine atoms.

Referring to the substituted or unsubstituted heterocyclic ring having a nitrogen atom as a hetero atom and in which the nitrogen atom is bonded to the naphthoxazine ring represented by R18 in the general formula (9), it is desired that the number of carbon atoms constituting the heterocyclic group is 2 to 10 and, preferably, 2 to 6. The ring may contain a hetero atom in addition to the nitrogen atom bonded to the naphthoxazine ring. Though there is no particular limitation, the hetero atom is preferably an oxygen atom, a sulfur atom or a nitrogen atom. As the aromatic hydrocarbon ring and the aromatic heterocyclic ring forming a condensed heterocyclic group upon being condensed with the heterocyclic group, there can be used an aromatic hydrocarbon ring and an aromatic heterocyclic ring having 6 to 10 carbon atoms. As these rings, there can be preferably used benzene rings, thiophene rings, furan rings and, particularly, benzene rings.

A known substituent can be used without limitation as a substituent for the heterocyclic group having the nitrogen atom as a hetero atom and is bonded to the naphthoxazine ring through the nitrogen atom or as a substituent for the condensed heterocyclic group formed by the condensation of the heterocyclic group with an aromatic hydrocarbon ring or an aromatic heterocyclic ring. From the standpoint of easy synthesis, the substituent will be an alkyl group having 1 to 4 carbon atoms, such as methyl group, ethyl group, isopropyl group, n-propyl group or t-butyl group, an alkoxyl group such as methoxy group, ethoxy group, isopropoxy group, n-propoxy group or t-butoxy group, or a halogen atom such as fluorine atom, chlorine atom or bromine atom.

As the substituted or unsubstituted heterocyclic ring having the nitrogen atom as a hetero atom and is bonded to the naphthoxazine ring through the nitrogen atom or as the condensed heterocyclic group formed by the condensation of the heterocyclic group with an aromatic hydrocarbon ring or an aromatic heterocyclic ring, there can be exemplified pyrrolidinyl group, piperidino group, hexamethyleneimino group, 2,2,6,6-tetramethylpiperidino group, morpholino group, 2,6-dimethylmorpholino group, N-methylpiperadinyl group, thiomorpholino group, indolyl group, 2-methylindolyl group, tetrahydroquinolyl group and aziridinyl group.

Concrete examples of the spirooxazine compound that can be preferably used for the photochromic composition of the present invention are as follows:
1) 1', 5'-dimethyl-6'-fluoro-6"-morpholinodispiro (cyclohexane-1,3'-(3H)indole-2'-(2H), 3"-(3H)naphtho(3, 2-a)(1, 4) oxazine, 2) 6'-fluoro-1'-methyl-8"-methoxy-6"-piperidinodispiro (cyclohexane-1,3,'-(3H)indole-2'-(2H),3"-(3H)naphtho(3, 2-a)(1, 4) oxazine,
3) 6'-fluoro-6"-morpholino-1'-neopentyldispiro (cyclohexane-1,3'-(3H)indole-2'-(2H),3"-(3H)naphtho(3, 2-a)(1, 4) oxazine,
4) 5', 7'-difluoro-1'-methyl-6"-morpholinodispiro (cyclohexane-1, 3'-(3H)indole-2'-(2H), 3"-(3H)naphtho (3,2-a)(1,4) oxazine,
5) 6'-fluoro-1'-(2-methyl)propyl-6"-morpholinodispiro (cyclohexane-1,3'-(3H)indole-2'-(2H), 3"-(3H)naphtho(3, 2-a)(1, 4) oxazine,
6) 6"-indolino-1', 5'-dimethyl-6'-fluorodispiro(cyclohexane-1,3'-(3H)indole-2'-(2H), 3"-(3H)naphtho(3, 2-a)(1, 4) oxazine, and
7) 5'-methyl-6'-fluoro-1-(2-methyl)propyldispiro (cyclohexane-1,3'-(3H)indole-2'-(2H), 3"-(3H)naphtho(3, 2-a)(1, 4) oxazine.

The above-mentioned spirooxazine compounds can be used in a single kind or being mixed together in two or more kinds at any ratio.

A fulgimide skeleton is possessed by the fulgimide compound that can be used in combination with the chromene composition of the present invention comprising the chromene compound represented by the general formula (1) and the chromene compound represented by the general formula (7). A known compound having photochromic his property can be used as the fulgimide compound without any limitation. A fulgimide compound represented by, for example, the following general formula (10) can be preferably used,

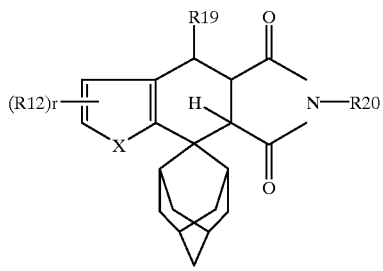

(10)

wherein R19 is an alkyl group, a cycloalkyl group, a substituted or unsubstituted aryl group, or a substituted or unsubstituted heteroaryl group, R20 is a cyano group, a cyanomethyl group or an m-cyanophenyl group, R21 is an alkyl group, a substituted or unsubstituted aryl group or a halogen atom, X is a sulfur atom or an oxygen atom, and r is an integer of 0 to 2 representing the number of the substituents R21 and when r is 2, R21 may be the same or different substituents.

As the alkyl groups represented by R19 and R21 in the above general formula (10), there can be used those alkyl groups having 1 to 4 carbon atoms, such as methyl group, ethyl group, n-propyl group, isopropyl group, n-butyl group and isobutyl group.

Though there is no particular limitation, the cycloalkyl group represented by R19 in the general formula (10) is the one having 3 to 6 carbon atoms, such as cyclopropyl group, cyclobutyl group, cyclopentyl group or cyclohexyl group.

As the aryl group represented by R19 in the general formula (10), there is generally used a phenyl group, though there is no particular limitation. A known substituent can be used as the one for the aryl group without limitation. Preferably, however, there is used an alkoxyl group having 1 to 4 carbon atoms, such as methoxy group, ethoxy group, n-propoxy group, isopropoxy group, n-butoxy group, isobutoxy group or t-butoxy group, an alkyl group having 1 to 4 carbon atoms, such as methyl group, ethyl group, isopropyl group, n-butyl group or t-butyl group, a halogen atom such as fluorine atom, chlorine atom or bromine atom, or a cyano group or a trifluoromethyl group. Though there is no particular limitation on the number of the substituents on the aryl group, it is desired that the number of the substituents is from 0 to 3 and, preferably, from 0 to 2 from the standpoint of easy synthesis.

As the heteroaryl group represented by R19 in the general formula (10), there is generally used a heteroaryl group such as thiophene ring, furan ring, benzothiophene ring or benzofuran ring though there is no particular limitation. A known substituent can be used as the one for the heteroaryl group without limitation. Preferably, however, there is used an alkoxyl group having 1 to 4 carbon atoms, such as methoxy group, ethoxy group, n-propoxy group, isopropoxy group, n-butoxy group, isobutoxy group or t-butoxy group, an alkyl group having 1 to 4 carbon atoms, such as methyl group, ethyl group, isopropyl group, n-butyl group or t-butyl group, a halogen atom such as fluorine atom, chlorine atom or bromine atom, or a cyano group or a trifluoromethyl group. Though there is no particular limitation on the number of the substituents on the heteroaryl group, it is desired that the number of the substituents is from 0 to 3 and, preferably, from 0 to 2 from the standpoint of easy synthesis.

As the aryl group represented by R21 in the general formula (10), there is generally used a phenyl group without any particular limitation. A known substituent can be used as the one for the aryl group without limitation. Preferably, however, there is used an alkoxyl group having 1 to 4 carbon atoms, such as methoxy group, ethoxy group, n-propoxy group, isopropoxy group, n-butoxy group, isobutoxy group or t-butoxy group, an alkyl group having 1 to 4 carbon atoms, such as methyl group, ethyl group, isopropyl group, n-butyl group, isobutyl group or t-butyl group, a halogen atom such as fluorine atom, chlorine atom or bromine atom, or a cyano group or a trifluoromethyl group. Though there is no particular limitation on the number of the substituents on the aryl group, it is desired that the number of the substituents is from 0 to 3 and, preferably, from 0 to 2 from the standpoint of easy synthesis.

In the general formula (10), r is an integer of 0 to 2 representing the number of the substituents R21, and which, preferably, is 0 or 1.

Concrete examples of the fulgimide compound that can be favorably used in the present invention are as follows:
1) N-cyanomethyl-6,7-dihydro-4-methyl-2-phenylspiro(5, 6-benzo[b]thiophenedicarboxyimide-7,2-tricyclo[3.3.1. $1^{3,7}$] decane),
2) N-cyanomethyl-6,7-dihydro-2-(4'-methoxypheny)-4-methylspiro(5,6-benzo[b]thiophenedicarboxyimide-7,2-tricyclo[3.3.1.$1^{3,7}$] decane),
3) N-cyano-6,7-dihydro-4-methyl-2-phenylspiro(5,6-benzo [b]thiophenedicarboxyimide-7,2-tricyclo[3.3.1.$1^{3,7}$] decane),
4) N-cyano-6,7-dihydro-4-methylspiro(5,6-benzo[b] furandicarboxyimide-7,2-tricyclo[3.3.1.$1^{3,7}$] decane), [3.3.1.$1^{3,7}$]
5) N-cyano-4-cyclopropyl-6,7-dihydrospiro(5,6-benzo[b] furandicarboxyimide-7,2-tricyclo[3.3.1.$1^{3,7}$] decane),
6) N-cyano-6,7-dihydro-4-methylspiro(5,6-benzo[b] thiophenedicarboxyimide-7,2-tricyclo[3.3.1.$1^{3,7}$] decane),
7) N-cyanomethyl-4-cyclopropyl-6,7-dihydrospiro(5,6-benzo[b]thiophenedicarboxyimide-7,2-tricyclo[3.3.1.$1^{3,}$ $_7$] decane), 8) N-cyanomethyl-4-cyclopropyl-6,7-dihydro-2-(4'-methoxyphenylspiro(5,6-benzo[b]thiophenedicarboxyimide-7,2-tricyclo[3.3.1.1$^{3,7}$] decane),
9) N-cyanomethyl-4-cyclopropyl-6,7-dihydro-2-phenylspiro(5,6-benzo[b]thiophenedicarboxyimide-7,2-tricyclo[3.3.1.1$^{3,7}$] decane), and
10) N-(3'-cyanophenyl)-6,7-dihydro-4-methyl-2-(4'-methoxyphenyl)spirobenzothiophenecarboxyimide-7,2'-tricyclo[3.3.1.1$^{3,7}$] decane).

The above-mentioned fulgimide compounds can be used in a single kind or being mixed in two or more kinds at any ratio.

In the photochromic composition of the present invention, there is no particular limitation on the amounts of blending the above-mentioned photochromic compounds, and the amounts may be suitably determined by taking the properties of the photochromic compounds into consideration. Described below are preferred amounts of blending the chromene compound represented by the general formula (1), chromene compound represented by the general formula (7), spirooxazine compound and fulgimide compound.

*Chromene compound represented by the general formula (1): 100 parts by weight.
*Chromene compound represented by the general formula (7): 10 to 1000 parts by weight, preferably, 17 to 1000 parts by weight, and more preferably, 17 to 500 parts by weight.
*Spirooxazine compound: 10 to 1000 parts by weight, preferably, 20 to 1000 parts by weight, and more preferably, 25 to 600 parts by weight.
*Fulgimide compound: 10 to 1000 parts by weight, preferably 20 to 1000 parts by weight, and more preferably, 25 to 600 parts by weight.

Upon blending the above-mentioned compounds in an amounts within the above-mentioned range, the photochromic composition of the present invention develops an intermediate color such as grey, amber or brown, which is preferred as a general photochromic lens, and is preferably used as a photochromic composition for photochromic lens.

When the photochromic compounds are mixed together as described above, furthermore, it often happens that the tone of the initial color greatly differs from the tone of when the color is developed to a saturated degree, since the color-developing sensitivities are different among the photochromic compounds. It is, however, possible to avoid such a problem by adjusting the kinds of the compounds and the mixing ratios.

The blending ratio of spirooxazine compound/fulgimide compound may differ depending upon the properties of the compounds and the amounts of addition, and is arbitrarily determined depending upon the object. From the standpoint of suppressing a change in the color tone after used for extended periods of time, it is desired that the blending ratio is not smaller than 2. From the standpoint of color-developing sensitivity, however, it is desired that the blending ratio is not larger than 1.

An ultraviolet ray-absorbing agent may be added to the photochromic composition of the present invention in order to suppress coloring after aged. As the ultraviolet ray-absorbing agent, there can be used those same as the ultraviolet ray-absorbing agents described in the section of the chromene composition of the present invention without any trouble.

There is no particular limitation on the preferred amount of blending the ultraviolet ray-absorbing agent. From the standpoint of suppressing the coloring after aged, however, it is desired to add the ultraviolet ray-absorbing agent in an amount of not smaller than 1 part by weight per 100 parts by weight of the photochromic composition. From the standpoint of suppressing a drop in the color density, it is desired to add the ultraviolet ray-absorbing agent in an amount of not larger than 500 parts by weight and, preferably, in an amount of 10 to 300 parts by weight per 100 parts by weight of the photochromic composition.

As required, furthermore, the photochromic composition of the present invention may be blended with various stabilizers and additives, such as antioxidizing agent, ultraviolet ray stabilizer, dye, pigment, coloring-preventing agent, antistatic agent, fluorescent dye, etc.

As the ultraviolet ray stabilizer, there can be preferably used a hindered amine photo-stabilizer, a hindered phenol photo-stabilizer or a sulfur-type antioxidizing agent. Though there is no particular limitation, the ultraviolet ray stabilizer is usually used in an amount of from 0.01 to 10 parts by weight and, preferably, from 0.1 to 10 parts by weight per 100 parts by weight of the photochromic composition.

The chromene compound represented by the general formula (1), chromene composition and photochromic composition of the present invention, exhibit favorable photochromic property even in a polymer. Such a polymer can be advantageously used as a photochromic glass and a photochromic lens.

As a polymer for dispersing the chromene compound, chromene composition or photochromic composition of the present invention, there can be used either a thermoplastic resin or a thermosetting resin. Between them, any thermoplastic resin can be used provided it permits the chromene compound, chromene composition or photochromic composition of the present invention to be homogeneously dispersed therein. For example, there can be preferably used a polymer, such as polymethyl acrylate, polyethyl acrylate, polymethyl methacrylate, polyethyl methacrylate, polystyrene, polyacrylonitrile, polyvinyl alcohol, polyacrylamide, poly(2-hydroxyethylmethacrylate), polydimethylsiloxane, polycarbonate, or poly(allyldiglycol carbonate), or a polymer obtained by copolymerizing the monomers that are the starting materials of these polymers.

As the thermosetting resin for dispersing the chromene compound, chromene composition or photochromic composition of the present invention, there can be used a known thermosetting resin without any limitation. There can be used, for example, an urethane resin obtained by the addition polymerization of a polyfunctional isocyanate with a polyfunctional mercapto compound or a polyfunctional hydroxy compound, an epoxy resin obtained by curing a polyfunctional epoxy compound, or a resin obtained by curing a polyfunctional radically polymerizable monomer.

There is no particular limitation on the method of dispersing the chromene compound, chromene composition or photochromic composition of the present invention in the polymer, and a general method can be employed. For example, there can be employed a method in which the thermoplastic resin and the chromene compound are kneaded together in a molten state and are dispersed in the resin, a method in which the chromene compound is melt-dissolved in the polymerizable monomer of the thermoplastic resin and the thermosetting resin and, then, a catalyst for polymerization is added to carry out the polymerization relying on heat or light, so that the chromene compound is dispersed in the resin, or a method in which the surfaces of the thermoplastic resin and the thermosetting resin are dyed with the chromene compound, so that the chromene compound is dispersed in the resins. Among these methods, it is desired to employ the method in which the chromene compound, chromene composition or photochromic composition of the present invention is mixed and dispersed in the polymerizable monomer which is then polymerized, from the standpoint of easy operation.

When the photochromic polymerizable composition is to be prepared by mixing the chromene compound, chromene composition or photochromic composition of the present invention and the polymerizable monomer together, it is desired that the compound or the composition is mixed in an amount of, usually;

(A) in the case of the chromene compound of the invention: from 0.001 to 10 parts by weight, preferably, from 0.01 to 1 part by weight and, more preferably, from 0.01 to 0.2 parts by weight;

(B) in the case of the chromene composition of the invention: from 0.001 to 10 parts by weight, preferably, from 0.005 to 1 part by weight and, more preferably, from 0.01 to 0.2 parts by weight;

(C) in the case of the photochromic composition of the invention: from 0.02 to 1 part by weight, preferably, from 0.05 to 0.5 parts by weight and, more preferably, from 0.10 to 0.25 parts by weight; per 100 parts by weight of the polymerizable monomer.

It is desired that the polymerizable monomer is a radically polymerizable monomer in order to avoid a drop in the photochromic property caused by the polymerizable group remaining after the polymerization. As the radically polymerizable monomer, there can be used a polymerizable monomer having a polymerizable group such as vinyl group, allyl group, acryloyl group or methacryloyl group. In order to obtain a favorable photochromic property, however, it is most desired to use a polymerizable monomer having an acryloyl group or a methacryloyl group.

Described below are concrete examples of the polymerizable monomer that can be favorably used in the present invention. As the polyfunctional radically polymerizable monomer having a vinyl group or an allyl group, there can be exemplified multi-valent allyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate, and trimethylolpropanetriallyl carbonate; multi-valent thioacrylic acid and multi-valent thiomethacrylic acid ester compounds such as 1,2-bis (methacryloylthio) ethane, bis(2-acryloylthioethyl)ether, and 1,4-bis(methacryloylthiomethyl) benzene; and divinyl benzene.

As the polyfunctional radically polymerizable monomer having an acryloyl group or a methacryloyl group (hereinafter simply referred to as polyfunctional (meth) acrylate), there can be used a monomer represented y the following general formula (11),

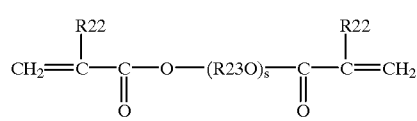

(11)

wherein R22 is a hydrogen atom or a methyl group, and R23 is an alkylene group having 1 to 4 carbon atoms or is represented by the following formula (12),

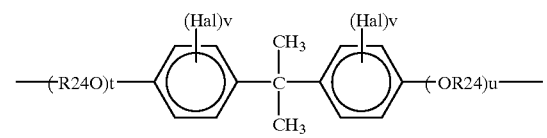

(12)

wherein R24 is an alkylene group having 1 to 4 carbon atoms, Hal is a halogen atom, t and u are integers of 0 to 10, and v is an integer of 0 to 4 representing the number of substitutions with halogen atoms, and s is an integer of 1 to 10, or a monomer presented by the following general formula (13),

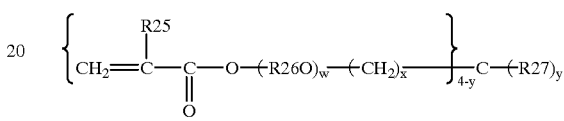

(13)

wherein R25 is a hydrogen atom or a methyl group, R26 is an ethylene group or a propylene group, w is an integer of 0 to 10, x is 0 or 1, y is an integer of 0 to 2, and R27 is a hydrogen atom, a hydroxymethyl group or an alkyl group having 1 to 4 carbon atoms.

As the alkylene group having 1 to 4 carbon atoms represented by R23 in the above general formula (11), there can be exemplified a methylene group, ethylene group, propylene group, isopropylene group, butylene group, isobutylene group, trimethylene group and tetramethylene group. In the above-mentioned formula (12), furthermore, the alkylene group having 1 to 4 carbon atoms represented by R24 is the same as the one defined by R23. In the formula (12), Hal is a halogen atom which will be a bromine atom, a chlorine atom or a fluorine atom.

In the general formula (13), R27 is a hydrogen atom, a hydroxymethyl group or an alkyl group having 1 to 4 carbon atoms. As the alkyl group having 1 to 4 carbon atoms, there can be exemplified a methyl group, ethyl group, propyl group, n-butyl group and tert-butyl group.

In the present invention, the word "(meth)acrylate" is a general term to stand for methacrylate compounds and acrylate compounds.

Depending upon the object, furthermore, the monofunctional (meth)acrylate monomer may be added to the above-mentioned polyfunctional radically polymerizable monomer to obtain a copolymer thereof. A monofunctional (meth) acrylate monomer that can be favorably used is represented by the following general formula (14),

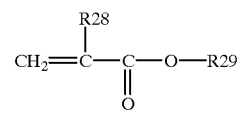

(14)

wherein R28 is a hydrogen atom or a methyl group, and R29 is an alkyl group having 1 to 4 carbon atoms which may be substituted with a hydroxyl group, an aryl group having 6 to 10 carbon atoms which may be substituted with a halogen atom, or an aralkyl group having 7 to 10 carbon atoms which may be substituted with a halogen atom.

As the alkyl group having 1 to 4 carbon atoms that may be substituted with a hydroxyl group represented by R29 in the above-mentioned general formula (14), there can be exemplified a methyl group, ethyl group, propyl group, butyl group, hydroxyethyl group and hydroxypropyl group. As the aryl group having 6 to 10 carbon atoms that may be substituted with a halogen atom, there can be exemplified a phenyl group, naphthyl group, chlorophenyl group, dichlorophenyl group, trichlorophenyl group, chloronaphthyl group and trichloronaphthyl group. As the aralkyl group having 7 to 10 carbon atoms that may be substituted with a halogen atom, there can be exemplified a benzyl group, phenethyl group, chlorobenzyl group, bromobenzyl group, trichlorobenzyl group and tribromobenzyl group.

Described below are concrete examples of the compounds that can be favorably used as polyfunctional (meth)acrylates represented by the above-mentioned general formulas (11) and (13):

ethylene glycol di(meth)acrylate,
diethylene glycol di(meth)acrylate,
triethylene glycol di(meth)acrylate,
tetraethylene glycol di(meth)acrylate,
polyethylene glycol di(meth)acrylate,
propylene glycol di(meth)acrylate,
dipropylene glycol di(meth)acrylate,
tripropylene glycol di(meth)acrylate,
tetrapropylene glycol di(meth)acrylate,
polypropylene glycol di(meth)acrylate,
1,6-hexanediol di(meth)acrylate,
neopentyl glycol di(meth)acrylate,
ethylene glycol bisglycidyl methacrylate,
2,2'-bis(4-methacryloyloxyethoxyphenyl)propane,
2,2-bis(4-methacryloyloxyethoxyphenyl)propane,
2,2-bis(4-acryloyloxyethoxyphenyl)propane,
2,2-bis(4-methacryloyloxypolyethoxyphenyl)propane,
2,2-bis(4-acryloyloxypolyethoxyphenyl) propane,
2,2-bis(3,5-dibromo-4-ethacryloyloxyethoxyphenyl) propane,
2,2-bis(3,5-dibromo-4-acryloyloxyethoxyphenyl) propane,
trimethylolpropane tri(meth)acrylate, and
pentaerythritol tetra(meth)acrylate.

These polyfunctional (meth)acrylates may be used in one kind or in two or more kinds being mixed together.

Concrete examples of the compound that can be favorably used as the monofunctional (meth)acrylate monomer represented by the general formula (14) include methyl(meth) acrylate, ethyl(meth)acrylate, butyl(meth)acrylate, benzyl (meth)acrylate, phenyl(meth)acrylate, 2-hydroxyethyl (meth)acrylate and tribromophenyl(meth)acrylate. These monofunctional (meth)acrylate monomers may be used in one kind or in two or more kinds being mixed together.

When an α-methylstyrene dimer is added, the chromene compound, the chromene composition or the photochromic polymerizable composition containing the photochromic composition and the polymerizable monomer of the present invention, exhibits improved moldability when it is cured and makes it possible to obtain a polymer maintaining a further improved yield. By adding a monofunctional radically polymerizable monomer having a polymerization-adjusting function such as α-methylstyrene, the moldability is further improved. It is therefore desired that the photochromic polymerizable composition contains 0.1 to 2 parts by weight of the α-methylstyrene dimer, 0 to 15 parts by weight of the α-methylstyrene, and 0.001 to 10 parts by weight of the chromene compound, chromene composition or photochromic composition represented by the general formula (1) of the present invention per 100 parts by weight of the polymerizable monomer excluding the α-methylstyrene diameter and α-methylstyrene.

When a compound having at least one epoxy group and radically polymerizable groups in one molecule thereof is added to the photochromic polymerizable composition, furthermore, durability of the photochromic property is improved.

As the compound having at least one epoxy group and radically polymerizable groups in one molecule thereof, there can be preferably used a compound having one epoxy group and one or more radically polymerizable groups in one molecule thereof. As the radically polymerizable group, there can be generally used a vinyl group, allyl group, acryloyl group or methacryloyl group. To obtain a good photochromic property, however, an acryloyl group or a methacryloyl group is preferably used. The compound having at least one epoxy group and radically polymerizable groups in one molecule that can be preferably used in the present invention, can be represented by the following general formula (15),

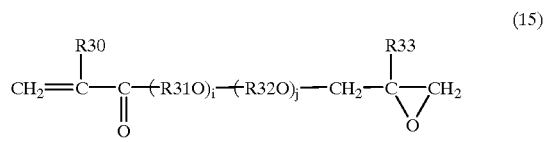

(15)

wherein R30 and R33 are independent from each other and are hydrogen atoms or methyl groups, R31 and R32 may be different from each other and are alkylene groups having 1 to 4 carbon atoms which may be substituted with a hydroxyl group, or groups represented by the following formula,

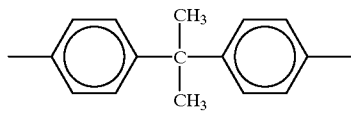

and i and j are 0 or 1 independently from each other.

As the alkylene groups represented by R31 and R32 in the above general formula (15), there can be exemplified methylene groups, ethylene groups, propylene groups, isopropylene groups, butylene groups, isobutylene groups, trimethylene groups and tetramethylene groups. These groups may be substituted with a hydroxyl group.

Described below are concrete examples of the compound that can be used as a compound having at least one epoxy group and radically polymerizable groups in one molecule thereof.

Acrylic ester compounds and methacrylic ester compounds such as:

glycidyl(meth)acrylate,
β-methylglycidyl(meth)acrylate, bisphenol A-monoglycidylether-(meth)acrylate,
4-glycidyloxybutyl(meth)acrylate,
3-(glycidyl-2-oxyethoxy)-2-hydroxypropyl(meth) acrylate,
3-(glycidyloxy-1-isopropyloxy)-2-hydroxypropyl(meth) acrylate, and
3-(glycidyloxy-2-hydroxypropyloxy)-2-hydroxypropyl (meth)acrylate.

Among them, the glicidyl(meth)acrylate is preferred from the standpoint of durability in the photochromic action.

It is desired that the compound having at least one epoxy group and radically polymerizable groups in one molecule thereof is blended in an amount of, usually, 1 to 30 parts by weight and, preferably, 1 to 10 parts by weight per 100 parts by weight of the polymerizable monomer or, preferably, per 100 parts by weight of the radically polymerizable monomer or, more preferably, per 100 parts by weight of the polyfunctional and/or monofunctional (meth)acrylate monomer.

There is no particular limitation on the method of preparing the photochromic polymerizable composition of the present invention, and the components may be mixed together in any order.

There is no particular limitation on the method of polymerization for obtaining a polymer from the photochromic polymerizable composition of the present invention, and any known radical polymerization method may be employed. The polymerization is conducted by using various radical polymerization initiators such as peroxides or azo compounds, or by being irradiated with ultraviolet rays, α-rays, β-rays or γ-rays, or by using both of them. A typical polymerization method may be a cast polymerization in which the photochromic curing composition of the present invention containing a radical polymerization initiator is injected into a mold held by an elastomer gasket or by a spacer, and is polymerized in a heated furnace and is, then, taken out.

There is no particular limitation on the radical polymerization initiator, and any known compound can be used. Representative examples include diallyl peroxides such as benzoyl peroxide, p-chlorobenzoyl peroxide, decanoyl peroxide, lauroyl peroxide and acetyl peroxide; peroxy esters such as t-butylperoxy-2-ethylhexanate, t-butylperoxyneodecanate, cumylperoxyneodecanate, t-butylperoxybenzoate, t-butylperoxyisobutylate, and 1,1,3, 3,-tetramethylbutylperoxy-2-ethylhexanate; percarbonates such as diisopropylperoxycarbonate, and di-sec-butylperoxydicarbonate; and azo compounds such as azobisisobutylonitrile and the like. Among them, it is desired to use the t-bgtylperoxyneodecanate, t-butylperoxyneodecanate/t-butylperoxyisobutylate, or t-butylperoxyneodecanate1,1,3,3-tetramethylbutylperoxy-2-ethylhexanate in combination from the standpoint of polymerization efficiency and hardness of the polymer.

The amount of the radical polymerization initiator that is used varies depending upon the polymerization conditions, kind of the initiator and composition of the radically polymerizable monomer, and cannot be exclusively determined. Generally, however, the radical polymerization initiator is used in an amount of from 0.001 to 10 parts by weight and, preferably, from 0.01 to 5 parts by weight per 100 parts by weight of the whole polymerizable monomers.

Among the polymerization conditions, the polymerization temperature differs depending upon the polymerizable monomer that is used and the kind of the radical polymerization initiator, and cannot be exclusively determined. Generally, however, a so-called taper-type two-stage polymerization is carried out, in which the polymerization starts at a relatively low temperature which is then gradually elevated, and the polymer is cured at a high temperature at the end of the polymerization. The polymerization time, too, varies depending upon a variety of factors like the polymerization temperature. It is therefore desired to determine an optimum polymerization time depending upon the conditions. Generally, however, it is desired that the polymerization is completed in 2 to 40 hours.

Industrial Applicability

The chromene compound represented by the above-mentioned general formula (1) of the present invention exhibits a large fading rate in a solution or in a high-molecular solid matrix compared with the conventional chromene compounds, and exhibits less color after aged and increased durability in the photochromic property.

Therefore, the chromene compound of the present invention can be used over a wide range as a photochromic material. For example, it can be used as various memory materials to substitute for a silver salt photosensitive material, i.e., used as a copying material, a photosensitive material for printing, a memory material for cathode-ray tubes, a photosensitive material for laser, a photosensitive material for holography, etc. Furthermore, the photochromic material using the chromene compound of the present invention can be utilized as a material for photochromic lenses, as a material for optical filters, as a display material, as a material for actinometers and as a material for ornamental use. When used for a photochromic lens, for example, any method can be used without limitation provided it makes it possible to obtain a uniform dimming performance. Concretely speaking, there can be employed a method in which a polymer film containing the photochromic material of the present invention homogeneously dispersed therein is sandwiched in the lens, a method in which the chromene compound of the present invention is dispersed in the polymerizable monomer and is polymerized according to a predetermined method, or a method in which the chromene compound is dissolved in, for example, a silicone oil, and the surfaces of the lens are impregnated with the compound at 150 to 200° C. for 10 to 60 minutes and are coated with a curing substance thereby to obtain a photochromic lens. There can be further employed a method in which the polymer film is applied onto the surfaces of the lens, and the surfaces are coated with a curing substance to obtain a photochromic lens.

The chromene compound of the present invention exhibits a high fading rate in a solution or in a high-molecular solid matrix, and less color after aged and increased durability in the photochromic property. By using the chromene compound of the present invention and the chromene compound represented by the general formula (7) in combination, furthermore, there is obtained a chromene composition exhibiting a high color-developing sensitivity, a large fading rate, suppressing the initial color and exhibiting less color after aged. By using the chromene compound of the present invention, chromene compound represented by the general formula (7), spirooxazine compound and fulgimide compound in combination, furthermore, there is obtained a photochromic composition exhibiting mixed colors, which is initially colored relatively less, exhibits color uniformly, and is less colored after aged. For example, the photochromic lens using the chromene compound of the present invention exhibits a small difference between the tone of initial color outdoors and the tone of color developed to a saturated degree, exhibits a large color density, exhibits a small change in the hue in the fading step when a person has returned from the outdoors into the indoors, and is less colored after used for extended periods of time and is aged.

EXAMPLES

The invention will now be described in further detail by way of Examples to which only, however, the invention is in no way limited. In Examples, "parts" are all "parts by weight". Described below are abbreviations of the compounds appearing in Examples and in Comparative Examples.

1. Radically polymerizable monomers.

3PG: Tripropylene glycol dimethacrylate (trade name: NK Ester 3PG, manufactured by Shin-Nakamura Kagaku Co.).

3G: Triethylene glycol dimethacrylate (trade name: NK Ester 3G, manufactured by Shin-Nakamura Kagaku Co.).

4G: Tetraethylene glycol dimethacrylate (trade name: NK Ester 4G, manufactured by Shin-Nakamura Kagaku Co.).

BPE-100N: 2,2-bis(4-methacryloyloxyethoxyphenyl) propane (trade name: NK Ester BPE-100, manufactured by Shin-Nakamura Kagaku Co.)

MS: α-Methylpsyrena

MSD: α-Methylstyrene dimer

HEMA: 2-Hydroxyethyl methacrylate

BZMA: Benzyl methacrylate

GMA: Glycidyl methacrylate

2. Radical Polymerization Initiators.

Perbutyl ND: t-Butylperoxyneodecanate (trade name: Perbutyl ND, manufactured by Nippon Yushi Co.).

Perocta O: 1,1,3,3-Tetramethylbutylperoxy-2-ethylhexanate (trade name: Perocta O, manufactured by Nippon Yushi Co.).

3. Ultraviolet ray-absorbing agents [hereinafter abbreviated as UVA].

Tinubin P: 2-(5-Methyl-2-hydroxyphenyl)benzotriazole (manufactured by Nippon Chiba Geigy Co.).

Sumisorb 110 (manufactured by Sumitomo Kagaku Kogyo Co.).

4. Photochromic compounds.

4-1. Chromene compounds (hereinafter often referred to as component (A)) represented by the general formula (1).

AC1) 5-Isopropyl-2,2-diphenyl-2H-benzo(h)chromene.

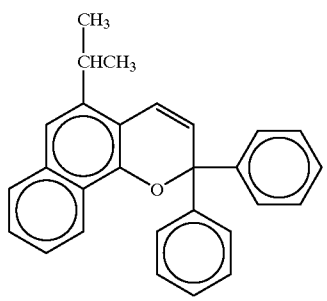

AC2) 5-t-Butyl-2,2-diphenyl-2H-benzo(h)chromene.

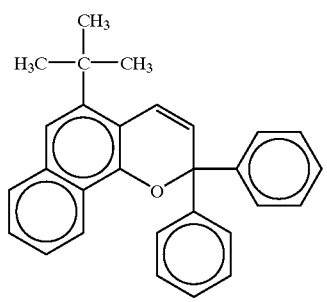

AC3) 5-Isopropyl-2,2-bis(3-fluoro-4-methoxyphenyl)-2H-benzo(h)chromene.

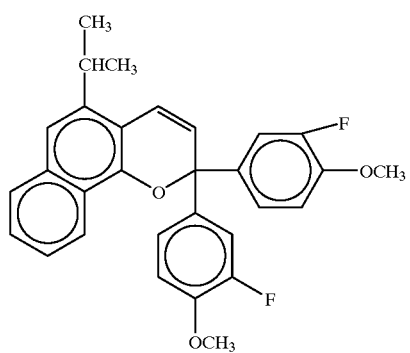

AC4) 5-Methyl-2,2-bis(4-methoxyphenyl)-2H-benzo(h)chromene.

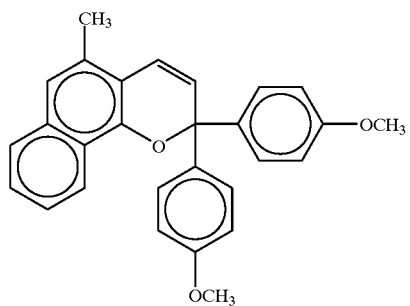

AC5) 5-Isopropyl-2-(4-methoxyphenyl)-2-(4-trifluoromethoxyphenyl)-2H-benzo(h)chromene.

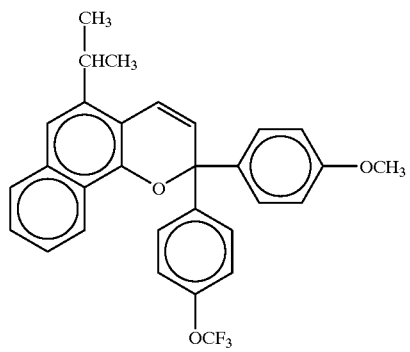

AC6) 5-Isopropyl-2-phenyl-2-(4-trifluoromethoxyphenyl)-2H-benzo(h)chromene.

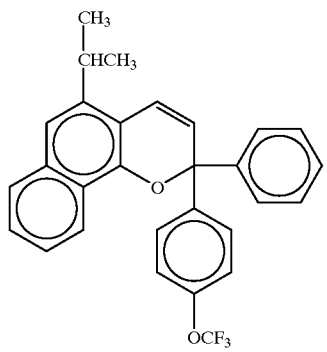

4-2. Chromene compounds (hereinafter often referred to as component (B)) represented by the general formula (7).

BC1) 6-Morpholino-3,3-bis(3-fluoro-4-methoxyphenyl)-3H-benzo(f)chromene.

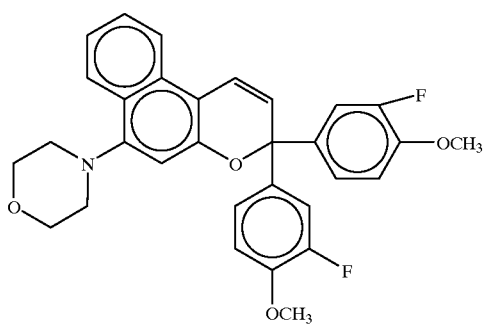

BC2) 6-Morpholino-3-(4-methoxyphenyl)-3-(4-trifluoromethoxyphenyl)-3H-benzo(f)chromene.

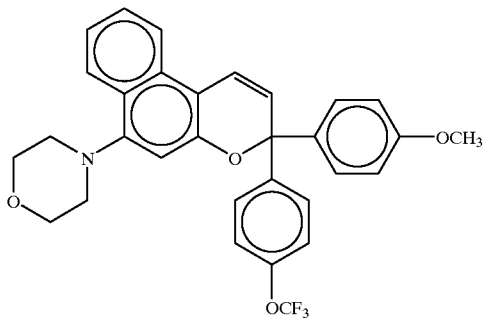

BC3) 6-Piperidino-3-methyl-3-(2-naphthyl)-3H-benzo(f) chromene.

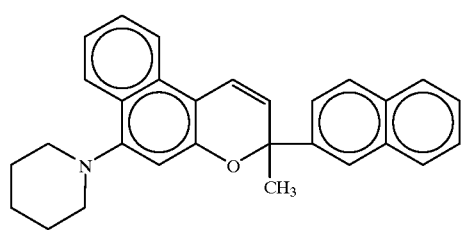

BC4) 6-Hexamethyleneimino-3-methyl-3-(4-methoxyphenyl)-3H-benzo(f)chromene.

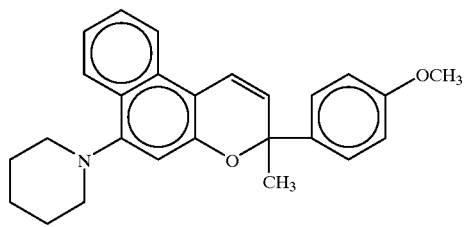

BC5) 6-Morpholino-3,3-bis(4-methoxyphenyl)-3H-enzo(f) chromene.

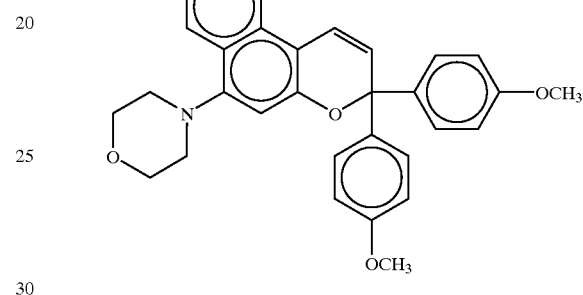

4-3. Other chromene compounds.

C1) Spiro(norbornane-2,2'-(2H)benzo(h)chromene).

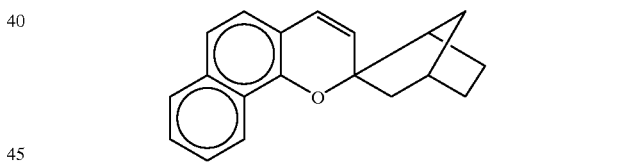

C2) 5-Ethoxycarbonyl-6-methyl-2,2-diphenyl-2H-benzo (h) chromene.

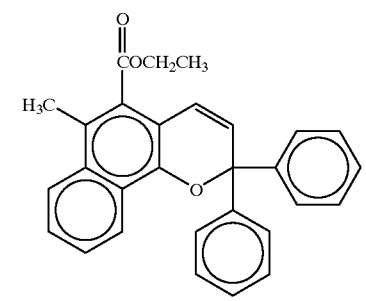

C3) 5,6-Dimethyl-2,2-diphenyl-2H-benzo(h)chromene.

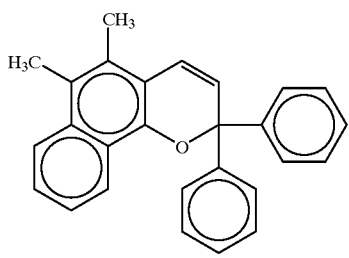

C4) 3,3-Diphenyl-3H-benzo(f)chromene.

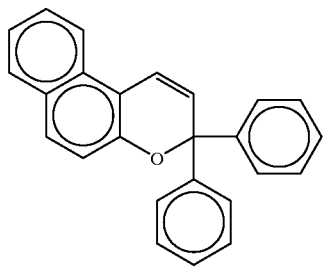

5. Spirooxazine compounds (hereinafter often referred to as component (C)).

CO1) 1', 5'-Dimethyl-6'-fluoro-6"-morpholinodispiro(cyclohexane-1,3'-(3H)indole-21-(2H),3"-(3H)naphtho(3,2-a)(1,4)oxazine.

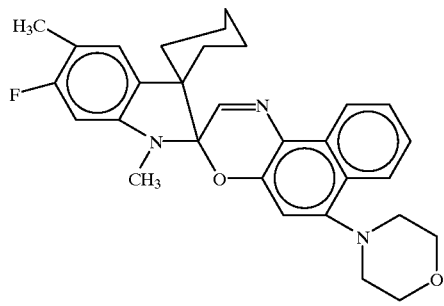

CO2) 6'-Fluoro-1'-(2-methyl)propyl-6"-morpholinodispiro(cyclohexane-1,3'-(3H)indole-2'-(2H),3"-(3H)naphtho(3,2-a)(1,4)oxazine.

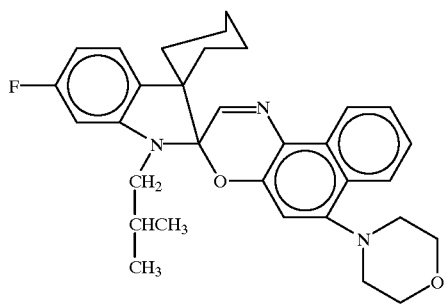

CO3) 3,3-Dimethyl-61-indolino-1-(2-methyl)propyl-spiro((3H)indole-2-(2H),3'-(3H)naphtho(3,2-a)(1,4)oxazine).

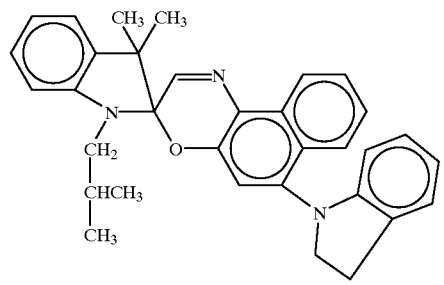

CO4) 5'-Methyl-6'-fluoro-1-(2-methyl)propyldispiro(cyclohexane-1,3'-(3H)indole-2'-(2H),3"-(3H)naphtho(3,2-a)(1,4)oxazine.

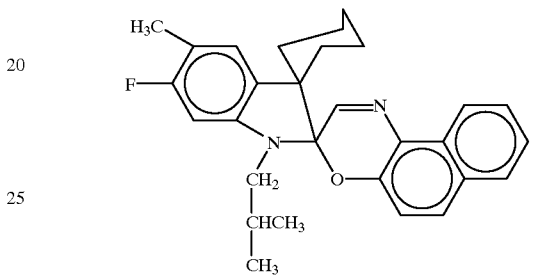

6. Fulgimide compounds (hereinafter often referred to as component (D)).

DF1) N-Cyanomethyl-4-cyclopropyl-6,7-dihydro-2-(4,-ethoxyphenyl)spiro(5,6-benzo[b]thiophenedicarboxyimide-7,2-tricyclo[3,3,1,1$^{3,7}$] decane).

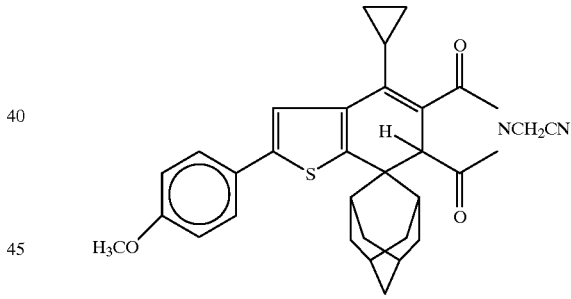

DF2) N-Cyanomethyl-4-cyclopropyl-6,7-dihydro-2-phenylspiro(5,6-benzo[b]thiophenedicarboxyimide-7,2-tricyclo[3.3.1.1$^{3,7}$] decane).

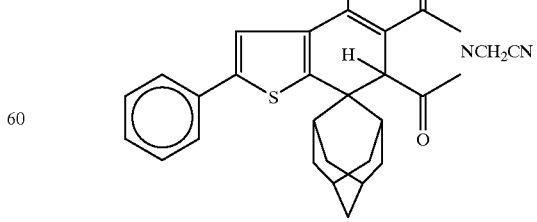

DF3) N-(3'-cyanophenyl)-6,7-dihydro-4-methyl-2-(4'-methoxyphenyl)spirobenzothiophenecarboxyimide-7,2'- tricyclo[3,3,1,1$^{3,7}$] decane).

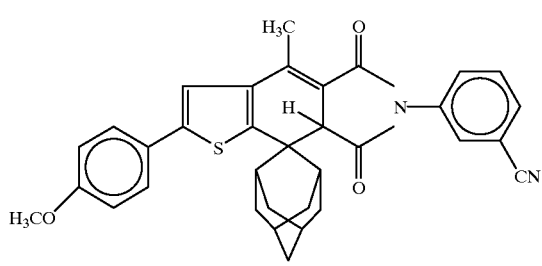

DF4) N-Cyanomethyl-6,7-dihydro-2-(4'-methoxyphenyl)-4-methylspiro(5,6-benzo[b]thiophenedicarboxyimide-7,2-tricyclo[3,3,1,1$^{3,7}$] decane).

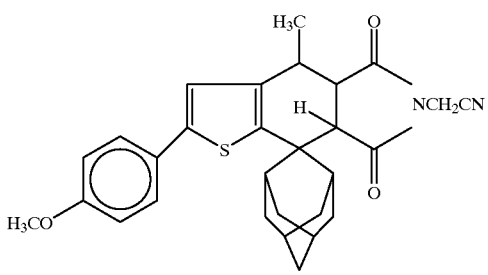

DF5) N-Cyanomethyl-6,7-dihydro-4-methyl-2-phenylspiro(5,6-benzo[b]thiophenedicarboxyimide-7,2-tricyclo[3,3,1,$^{3,7}$] decane).

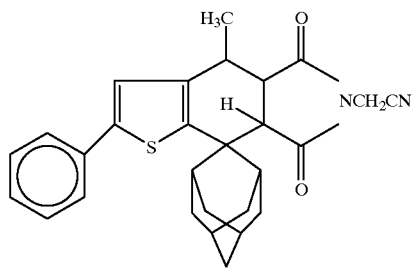

Example 1.

2.00 Grams (0.01 mol) of a compound of the following formula,

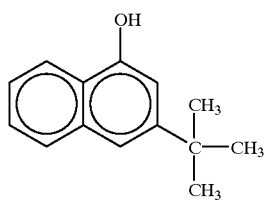

and 2.08 g (0.01 mol) of a compound of the following formula,

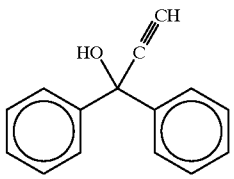

were dissolved in 50 ml of toluene, followed by the addition of 0.05 g of a p-toluenesulfonic acid, and the mixture was refluxed for 2 hours. After the reaction, the solvent was removed, and the reaction product was refined by the chromatography on a silica gel to obtain 1.17 g of a pale yellow powdery product.

Elemental analysis of the product showed C89.21%, H6.75%, and O4.15%, which were in very good agreement with C89.19%, H6.71%, and O4.10% calculated from $C_{29}H_{26}O$.

Measurement of the proton nuclear magnetic resonance spectrum showed a peak 9H near δ1.0 to 2.0 ppm due to a proton of a methyl group of a tert-butyl group, and peaks 17H near δ5.5 to 9.0 ppm due to an aromatic proton and a proton of an alkene as shown in FIG. 1.

Moreover, measurement of the $^{13}$C-nuclear magnetic resonance spectrum showed a peak near δ110 to 160 ppm due to carbon of an aromatic ring, a peak near δ80 to 140 ppm due to carbon of an alkene, and a peak at δ20 to 30 ppm due to carbon of an alkyl.

From the above results, it was confirmed that the isolated product was a chromene compound represented by the following structural formula.

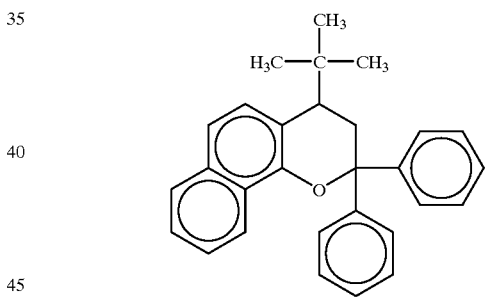

Example 2.

2.00 Grams (0.01 mol) of a compound of the following formula,

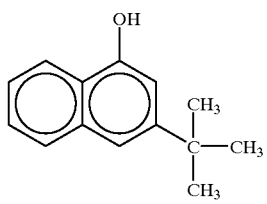

and 2.28 g (0.01 mol) of an ethyl orthotitanate were dissolved in 100 ml of toluene to carry out the reaction while distilling off the formed ethanol until the amount of distillate was 50 ml. After the reaction, 1.64 g (0.01 mol) of the following compound

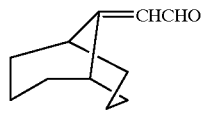

was added to carry out the reaction for another one hour at a refluxing temperature. After the reaction, the reaction product was added to 100 ml of water to separate the organic layer which was then dried on magnesium sulfate to remove the solvent. After the solvent has been removed, the reaction product was refined by the chromatography on a silica gel to obtain 1.21 g of a pale yellow powdery product.

Elemental analysis of the product showed C86.69%, H8.75%, and O4.68%, which were in very good agreement with C86.66%, H8.73%, and O4.62% calculated from $C_{25}H_{30}O$.

Measurement of the proton nuclear magnetic resonance spectrum showed peaks 23H near δ1.0 to 4.0 ppm due to a methyl group of a tert-butyl group and a proton of a bicyclononane, and peaks 7H near δ5.5 to 9.0 ppm due to an aromatic proton and a proton of an alkene.

Moreover, measurement of the $^{13}C$-nuclear magnetic resonance spectrum showed a peak near δ110 to 160 ppm due to carbon of an aromatic ring, a peak near δ80 to 140 ppm due to carbon of an alkene, and peaks near δ20 to 30 ppm due to carbon atoms of the tert-butyl group and the bicyclononane.

From the above results, it was confirmed that the isolated product was a chromene compound represented by the following structural formula.

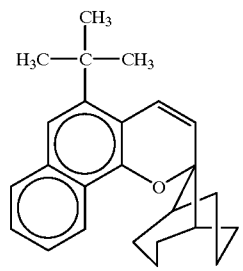

Examples 3 to 25.

The chromene compounds which are the products shown in Table 1 were synthesized by using starting materials shown in Table 1 in the same manner as in Example 1. The structures of the obtained products were analyzed by using the same structure confirmation means as that of Example 1, and it was confirmed that the products were chromene compounds having structural formulas shown in Table 1. Table 2 shows values of elemental analysis of these compounds, values calculated from the structural formulas of these compounds, and characteristic spectra of $^1H$-NMR spectra.

Example 26.

1.58 Grams (0.01 mol) of a naphthalene derivative of the following formula,

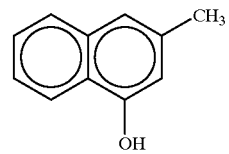

and 2.68 g (0.01 mol) of a propargyl alcohol derivative of the following formula,

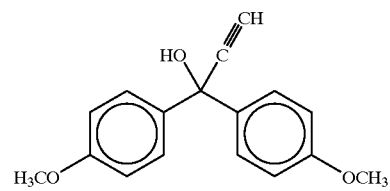

were dissolved in 50 ml of toluene, followed by the addition of 0.05 g of a p-toluenesulfonic acid, and the mixture was refluxed for 2 hours. After the reaction, the solvent was removed, and the reaction product was refined by the chromatography on a silica gel to obtain 1.1 g of a pale yellow powdery product, yield, 27%.

Elemental analysis of the product showed C82.30%, H5.87%, and O11.83%, which were in very good agreement with C82.35%, H5.88%, and O11.77% calculated from $C_{28}H_{24}O_3$.

Measurement of the proton nuclear magnetic resonance spectrum showed a peak 3H near δ2.0 ppm due to a proton of a methyl group, a peak 6H near δ4.0 ppm due to a proton of a methoxy group, and peaks 15H near δ5.5 to 9.0 ppm due to an aromatic proton and a proton of an alkene.

Moreover, measurement of the $^{13}C$-nuclear magnetic resonance spectrum showed a peak near δ110 to 160 ppm due to carbon of an aromatic ring, a peak near δ80 to 140 ppm due to carbon of an alkene, and a peak at δ20 to 30 ppm due to carbon of an alkyl.

From the above results, it was confirmed that the isolated product was a chromene compound represented by the following structural formula.

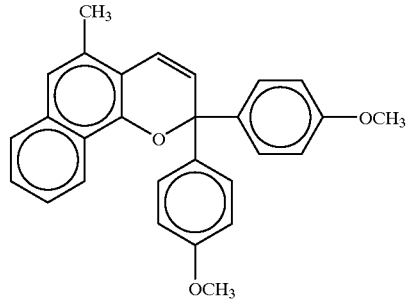

Examples 27 to 41.

The chromene compounds which are the products shown in Table 3 were synthesized by using starting materials shown in Table 3 in the same manner as in Example 26. The structures of the obtained products were analyzed by using the same structure confirmation means as that of Example 26, and it was confirmed that the products were chromene compounds having structural formulas shown in Table 3. Table 4 shows values of elemental analysis of these compounds, values calculated from the structural formulas of these compounds, and characteristic spectra of $^1$H-NMR spectra.

Example 42.

0.04% by weight of the chromene compound obtained in Example 1 was added to 70 parts of 4G, 15 parts of 3G, 10 parts of GMA, 5 parts of HEMA and 1 part of perbutyl ND, and was mixed together to a sufficient degree. The mixture solution was poured into a mold constituted by a glass plate and a gasket of an ethylene/vinyl acetate copolymer, and was cast-polymerized. By using an air furnace, the polymerization was conducted in a manner that the temperature was gradually raised from 30° C. to 90° C. over a period of 18 hours, and was held at 90° C. for 2 hours. After the polymerization, the polymer was taken out from the glass mold.

By using a xenon lamp, L-2480 (300 W) SHL-100, manufactured by Hamamatsu Photonics Co., the obtained polymer (2 mm thick) was irradiated with a beam of an intensity of 365 nm=2.4 mW/cm$^2$ and 245 nm=24 µW/cm$^2$ on the surface of the polymer for 120 seconds through an aero-mass filter (manufactured by Corning Co.) at 20° C.±1° C. to develop color and to measure the photochromic properties which were expressed in the following manner.

1 Maximum absorption wavelength (λmax): λmax of the polymer after it has developed color was found by using a spectrophotometer (instantaneous multi-channel photo-detector, MCPD1000) manufactured by Otsuka Denshi Kogyo Co.

2 Initial color ( ε(0)): Absorbency of the polymer in a non-irradiated state at a wavelength same as the maximum absorption wavelength of when it is irradiated with light.

3 Color density (–)=ε(120)–ε(0). ε(120): Absorbency of the polymer at a maximum absorption wavelength after it was irradiated for 120 seconds under the above-mentioned conditions.

4 Color-developing sensitivity (–/min.)=Saturated color density/xenon irradiation time.

Rate of increase in the color density per a unit time until the color density is saturated.

5 Color fading rate [t1/2 (min.)]=time required until the absorbency of the polymer drops down to one-half of [ε(120)–ε(0)] after irradiated for 120 seconds.

In order to promote the aging, furthermore, the following testing was conducted. That is, the obtained photochromic polymer was irradiated with sunlight for 30 minutes to develop color, and its color was permitted to fade for one hour in the light of a fluorescent lamp. This cycle was repeated three times a day for a total of 10 days.

The photochromic properties before and after aged were evaluated by evaluating the color densities before and after aged. The initial color density (T0) and the color density (T30) ten days after the aging promotion testing were measured, and the durability was expressed as described below.

6 Durability (%)=(T0/T30)×100

Furthermore, the coloring degrees of before developing color were measured before and after aged by using a color difference meter (SM-4) manufactured by Suga Shikenki Co.

7 Coloring degree before being aged=YI(0).

8 Change in the coloring degree (ΔYI)=YI(10)–YI(0)

YI(10): coloring degree after aged

Table 5 shows the measured results of maximum absorption wavelengths, color densities, fading rates, changes in the coloring degrees and durabilitys.

Examples 43 to 82 and Comparative Examples 1 to 6.

Photochromic polymers were prepared in the same manner as in Example 42 but using the chromene compounds obtained in Examples 2 to 41, and their maximum absorption wavelengths, color densities, fading rates, changes in the coloring degrees and durabilitys were measured. The results were as shown in Table 5.

For the purpose of comparison, furthermore, the compounds represented by the following formulas (a), (b), (c), (d), (e) and (f) were measured for their maximum absorption wavelengths, color densities, fading rates, changes in the coloring degrees and durabilitys. The results were as shown in Table 5.

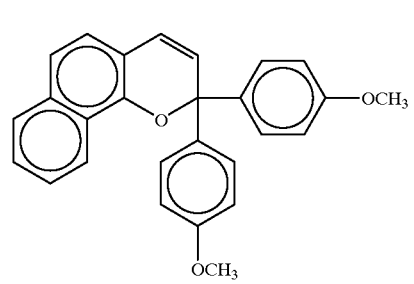

(a)

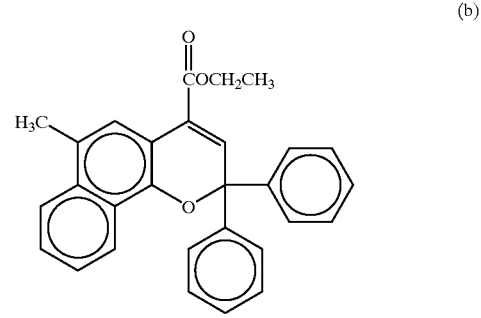

(b)

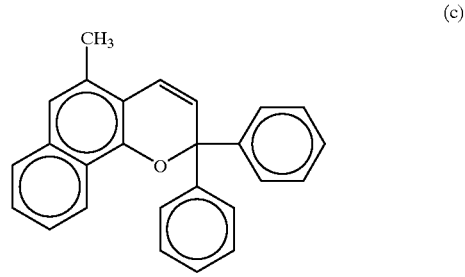

(c)

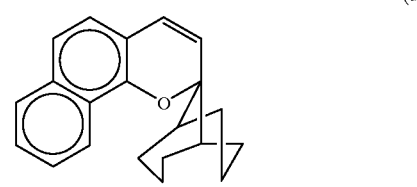

(d)

-continued

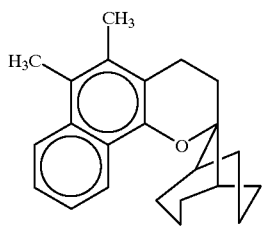

(e)

(f)

It will be understood from Table 5 that the chromene compounds of the present invention exhibit large fading rates, less color (change in the coloring degree) after aged and improved durability in the photochromic property compared to those of the chromene compounds of Comparative Examples 1 to 6.

Example 83.

The procedure was carried out in the same manner as in Example 42 but using 100 parts of AC1 and 133 parts of BC1, the sum of the amounts of AC1 and BC1 being 0.04% by weight. The obtained photochromic polymer was measured for its maximum absorption wavelength, initial color, color density, color-developing sensitivity, fading rate, durability and change in the coloring degree. The results were as shown in Table 6.

Examples 84 to 102.

The procedure was carried out in the same manner as in Example 83 but using the chromene compositions shown in Table 6. The results were as shown in Table 6.

Comparative Examples 7 to 10.

The procedure was carried out in the same manner as in Example 83 but using the known chromene compounds shown in Table 6 instead of the chromene compound used in Example 83.

Examples 103 to 106.

The procedure was carried out in the same manner as in Example 83 but using the polymerizable monomers and polymerization initiators shown in Table 7 instead of those used in Example 83. The results were as shown in Table 7.

It will be understood from Tables 6 and 7 that the chromene compositions of the present invention exhibit less initial colors, high color-developing sensitivities, high color densities, large fading rates, less colors after aged and improved balance in the photochromic properties compared with those of Comparative Examples 7 to 10.

Example 107.

To 100 parts by weight of a polymerizable monomer comprising 48 parts of BPE-100N, 35 parts of 3G, 8 parts of GMA, 8 parts of MS and 1 part of MSD, there were added 0.025 parts by weight of a chromene compound AC1 of the invention, 0.025 parts by weight of BC2 as photochromic compounds, 0.05 parts by weight of a spirooxazine compound CO1, 0.05 parts by weight of a fulgimide compound DF1, 0.5 parts by weight of a perbutyl ND as a polymerization initiator and 0.4 parts by weight of Perocta O. The mixture was mixed well. The mixture solution was poured into a mold constituted by a glass plate and a gasket of an ethylene/vinyl acetate copolymer, and was cast-polymerized. By using an air furnace, the polymerization was conducted in a manner that the temperature was gradually raised from 30° C. to 90° C. over a period of 18 hours, and was held at 90° C. for 2 hours. After the polymerization, the polymer was taken out from the glass mold.

The obtained polymer (2 mm thick) was caused to develop color outdoors, and tones of the developed color were observed by eyes 30 seconds and 15 minutes after it was brought to the outdoors, and uniformity in the step of developing color was evaluated. The polymer exhibited a difference in the color density when it was observed after 30 seconds and 15 minutes, but the color tone was the same, i.e., grey. Furthermore, the aging promoting testing was conducted in the same manner as in Example 42 to find a coloring degree (YI(0)) before aged and a change in the coloring degree ($\Delta Y$). The results were as shown in Table 8.

Examples 108 to 127.

The procedure was carried out in the same manner as in Example 107 but using the chromene compounds which are the components (A), chromene compounds which are the components (B), spirooxazine compounds and fulgimide compounds that are shown in Table 8. The results were as shown in Table 8.

Comparative Examples 11 to 14.

The procedure was carried out in the same manner as in Example 107 but using the chromene compounds shown in Table 8 instead of the chromene compound used in Example 107.

It will be understood from Table 8 that the photochromic compositions of the present invention develop color highly uniformly and are little colored even after aged. According to Comparative Examples 11 to 13, however, the tone of color is blue 0.5 minutes after the development of color and turns into grey or brown 15 minutes after the development of color. In the step of developing color, therefore, tone lacks uniformity. According to Comparative Example 14, the density of color developed by the chromene compound is so low that the color tone of spirooxazine and of fulgimide remains blue, making it difficult to produce mixed colors.

TABLE 1

| Ex. No. | Starting material | | Product | Yield (%) |
|---|---|---|---|---|
| 3 | (3-isopentyl-naphthalen-1-ol) | (1-(4-methoxyphenyl)-1-(furan-2-yl)prop-2-yn-1-ol) | (2H-naphtho[2,1-b]pyran with furan, 4-methoxyphenyl, and tert-pentyl substituents) | 10 |
| 4 | (3-sec-butyl-naphthalen-1-ol) | (1-(3-cyano-4-methoxyphenyl)-1-(4-methoxyphenyl)prop-2-yn-1-ol) | (2H-naphtho[2,1-b]pyran with 3-cyano-4-methoxyphenyl, 4-methoxyphenyl, and sec-butyl substituents) | 30 |

TABLE 1-continued
| Ex. No. | Starting material | | Product | Yield (%) |
|---|---|---|---|---|
| 5 | 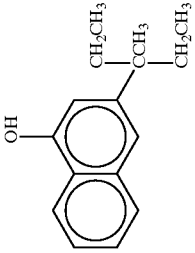 | 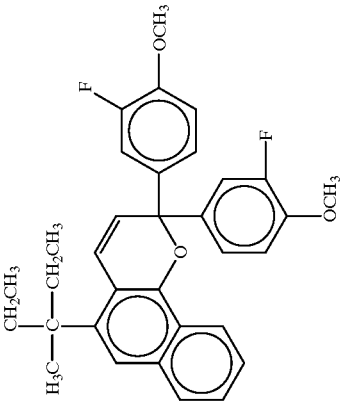 | 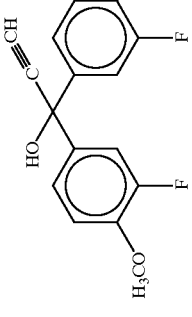 | 25 |
| 6 | 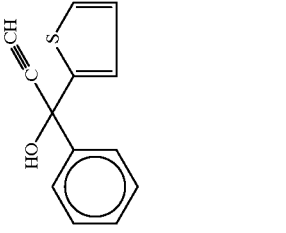 | 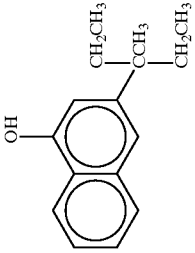 | 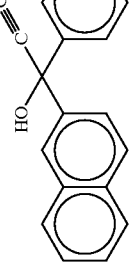 | 20 |
| 7 | | | | 30 |

TABLE 1-continued

| Ex. No. | Starting material | Product | Yield (%) |
|---|---|---|---|
| 8 | | | 15 |
| 9 | | | 5 |
| 10 | | | 5 |

TABLE 1-continued
| Ex. No. | Starting material | Product | Yield (%) |
|---|---|---|---|
| 11 | 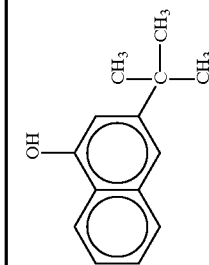 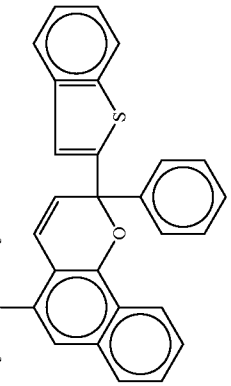 | 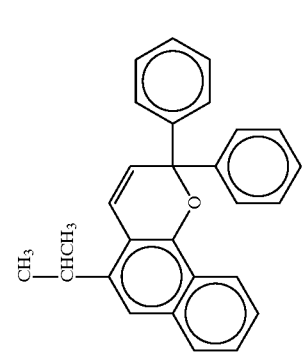 | 25 |
| 12 | 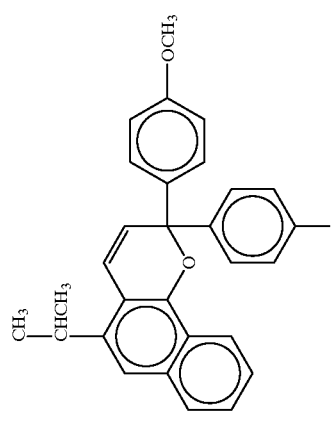 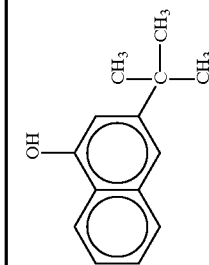 | 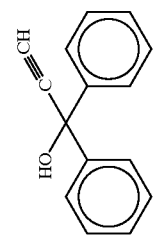 | 35 |
| 13 | 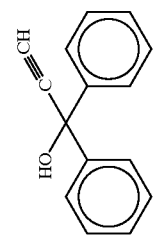 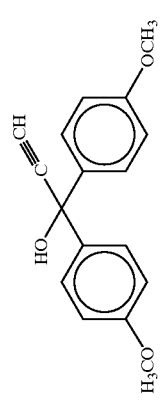 | 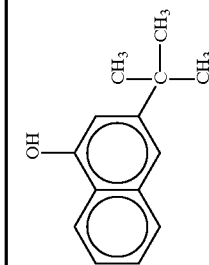 | 29 |

TABLE 1-continued
| Ex. No. | Starting material | | Product | Yield (%) |
|---|---|---|---|---|
| 14 | 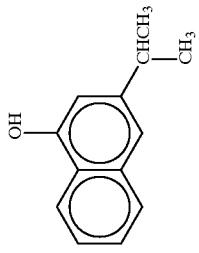 | 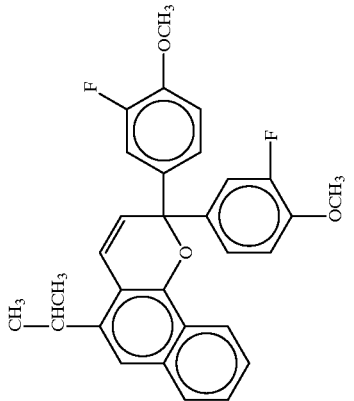 | 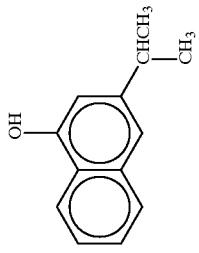 | 31 |
| 15 | 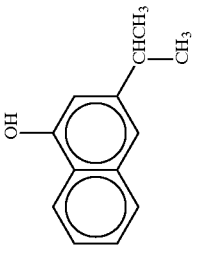 | 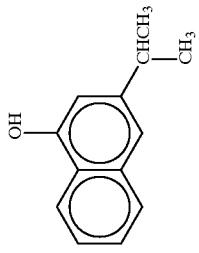 | 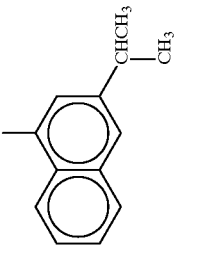 | 28 |
| 16 | | | | 25 |

TABLE 1-continued

| Ex. No. | Starting material | Product | Yield (%) |
|---|---|---|---|
| 17 | (naphthol with C(CH₃)₃ substituent) + HO-C(C≡CH)(Ph)(C₆H₄-OCF₃) | 2-phenyl-2-(4-trifluoromethoxyphenyl)-substituted naphthopyran with C(CH₃)₃ | 26 |
| 18 | (naphthol with C(CH₃)₃ substituent) + bicyclic =CHCHO | spiro-bicyclic naphthopyran with C(CH₃)₃ | 30 |
| 19 | (naphthol with CH(CH₃)₂ substituent) + bicyclic =CHCHO | spiro-bicyclic naphthopyran with CH(CH₃)₂ | 35 |

TABLE 1-continued

| Ex. No. | Starting material | | Product | Yield (%) |
|---|---|---|---|---|
| 20 | (naphthol with C(CH₃)₃ substituent) | (bicyclic dichloro CHCHO compound) | (chromene product with dichloro bicyclic group and C(CH₃)₃) | 10 |
| 21 | (naphthol with CH(CH₃)₂ substituent) | (bicyclic CHCHO compound with fused cyclopropane) | (chromene product with bicyclic group and CH(CH₃)₂) | 25 |
| 22 | (naphthol with C(CH₃)₃ substituent) | (bicyclic dichloro CHCHO compound with fused cyclopropane) | (chromene product with dichloro bicyclic group and C(CH₃)₃) | 10 |

TABLE 1-continued

| Ex. No. | Starting material | | Product | Yield (%) |
|---|---|---|---|---|
| 23 | [naphthol with CHCH₂CH₃/CH₃ group] | [bicyclic aldehyde CHCHO] | [chromene fused with naphthalene and bicyclic group, CH₃/CHCH₂CH₃ substituent] | 20 |
| 24 | [naphthol with C(CH₃)₃ group] | [adamantylidene CHCHO] | [chromene fused with naphthalene and adamantyl, (CH₃)₃C substituent] | 25 |
| 25 | [naphthol with CHCH₃/CH₃ group] | [adamantylidene CHCHO] | [chromene fused with naphthalene and adamantyl, CH₃/CHCH₃ substituent] | 30 |

TABLE 2

| | Elemental analysis values (%) | | | | | | | | 1H-NMR |
|---|---|---|---|---|---|---|---|---|---|
| | Found | | | | Calculated | | | | |
| Ex. No. | C | H | O | Others | C | H | O | Others | (ppm) |
| 3 | 82.07 | 6.70 | 11.29 | | 82.05 | 6.65 | 11.31 | | δ 1.0~4.0: 14H<br>δ 5.5~9.0: 14H |
| 4 | 80.85 | 6.20 | 10.11 | N: 2.90 | 80.82 | 6.15 | 10.09 | N: 2.95 | δ 1.0~4.0: 15H<br>δ 5.5~9.0: 14H |
| 5 | 77.05 | 6.30 | 9.35 | F: 7.42 | 77.02 | 6.27 | 9.33 | F: 7.38 | δ 1.0~4.0: 19H<br>δ 5.5~9.0: 13H |
| 6 | 81.75 | 6.13 | 4.08 | S: 8.14 | 81.78 | 6.10 | 4.03 | S: 8.08 | δ 1.0~2.0: 9H<br>δ 5.5~9.0: 15H |
| 7 | 90.15 | 6.20 | 3.77 | | 90.11 | 6.14 | 3.75 | | δ 1.0~2.0: 7H<br>δ 5.5~9.0: 19H |
| 8 | 84.13 | 6.46 | 6.61 | N: 2.93 | 84.09 | 6.43 | 6.59 | N: 2.88 | δ 1.0~4.0: 12H<br>δ 5.5~9.0: 19H |
| 9 | 71.31 | 4.99 | 7.95 | S: 15.88 | 71.26 | 4.98 | 7.91 | S: 15.85 | δ 1.0~2.0: 7H<br>δ 5.5~9.0: 13H |
| 10 | 83.15 | 6.57 | 10.42 | | 83.09 | 6.54 | 10.38 | | δ 1.0~4.0: 16H<br>δ 5.5~9.0: 14H |
| 11 | 83.41 | 5.92 | 3.63 | S: 7.20 | 83.37 | 5.87 | 3.58 | S: 7.18 | δ 1.0~2.0: 9H<br>δ 5.5~9.0: 17H |
| 12 | 89.40 | 6.44 | 4.17 | | 89.33 | 6.43 | 4.25 | | δ 5.9~9.0: 17H<br>δ 1.5~4.0: 7H |
| 13 | 82.48 | 6.44 | 11.07 | | 82.54 | 6.46 | 10.99 | | δ 5.9~9.0: 15H<br>δ 1.5~4.0: 13H |
| 14 | 76.20 | 5.53 | 10.38 | F: 7.98 | 76.26 | 5.55 | 10.16 | F: 8.04 | δ 5.9~9.0: 13H<br>δ 1.5~4.0: 13H |
| 15 | 73.51 | 5.15 | 9.88 | F: 11.48 | 73.46 | 5.14 | 9.79 | F: 11.61 | δ 5.9~9.0: 16H<br>δ 1.5~4.0: 7H |
| 16 | 78.58 | 5.00 | 7.00 | F: 11.66 | 75.64 | 5.03 | 6.95 | F: 11.61 | δ 5.9~9.0: 16H<br>δ 1.5~4.0: 7H |
| 17 | 76.00 | 5.33 | 6.84 | F: 12.18 | 75.94 | 5.31 | 6.74 | F: 12.00 | δ 5.9~9.0: 16H<br>δ 5.9~9.0: 7H |
| 18 | 86.71 | 8.28 | 5.10 | | 86.75 | 8.23 | 5.02 | | δ 0.5~2.0: 19H<br>δ 5.5~9.0: 7H |
| 19 | 86.88 | 7.91 | 5.30 | | 86.80 | 7.95 | 5.26 | | δ 0.5~2.0: 17H<br>δ 5.5~9.0: 7H |
| 20 | 71.30 | 6.30 | 4.15 | Cl: 4.16 | 71.32 | 6.25 | 4.13 | Cl: 4.13 | δ 0.5~2.0: 17H<br>δ 5.5~9.0: 7H |
| 21 | 86.66 | 8.55 | 4.85 | | 86.70 | 8.49 | 4.81 | | δ 0.5~2.0: 21H<br>δ 5.5~9.0: 7H |
| 22 | 72.35 | 6.83 | 3.91 | Cl: 17.10 | 72.29 | 6.79 | 3.85 | Cl: 17.07 | δ 0.5~2.0: 21H<br>δ 5.5~9.0: 7H |
| 23 | 86.65 | 8.75 | 4.65 | | 86.66 | 8.73 | 4.62 | | δ 0.5~2.0: 23H<br>δ 5.5~9.0: 7H |
| 24 | 87.15 | 8.45 | 4.50 | | 87.10 | 8.43 | 4.46 | | δ 0.5~2.0: 23H<br>δ 5.5~9.0: 7H |
| 25 | 87.20 | 8.20 | 4.69 | | 87.16 | 8.19 | 4.64 | | δ 0.5~2.0: 21H<br>δ 5.5~9.0: 7H |

TABLE 3
| Ex. No. | Starting material | | Product | Yield (%) |
|---|---|---|---|---|
| | Naphthol derivative | Propargyl alcohol derivative | | |
| 27 | 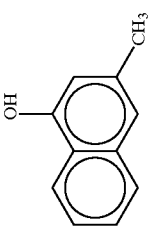 | 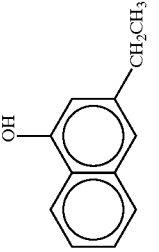 | 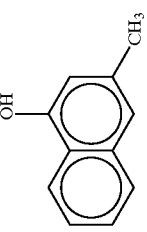 | 25 |
| 28 | 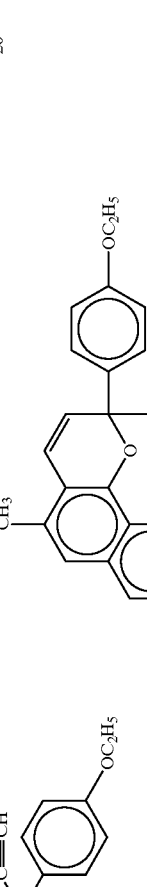 | 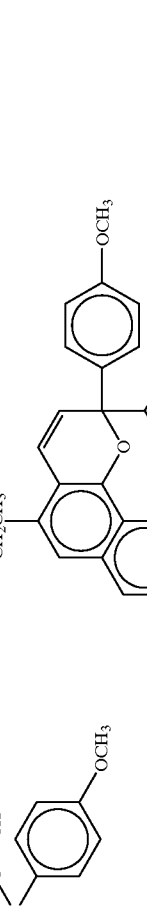 | 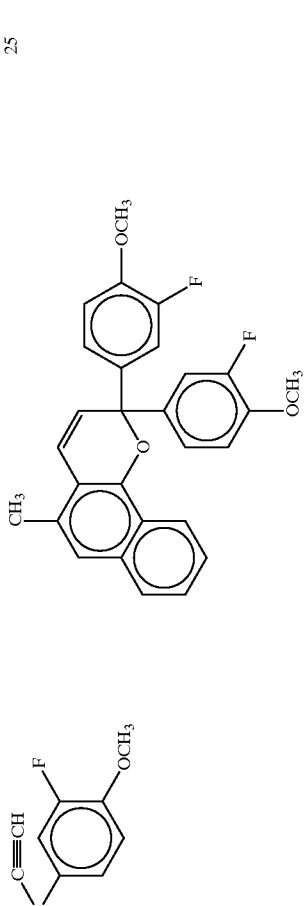 | 15 |
| 29 | 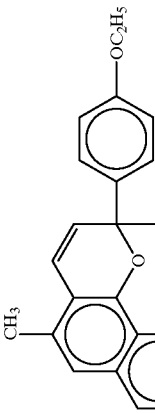 | 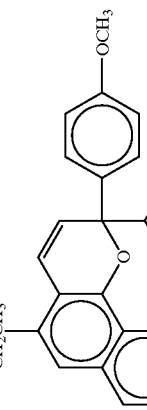 | 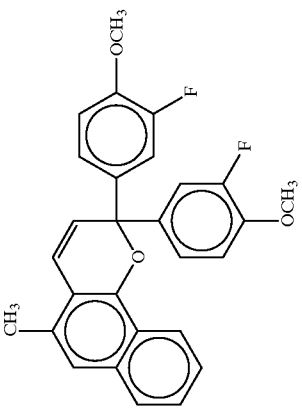 | 20 |

TABLE 3-continued

| Ex. No. | Starting material | | Product | Yield (%) |
|---|---|---|---|---|
| | Naphthol derivative | Propargyl alcohol derivative | | |
| 30 | 4-hydroxy-3-methylnaphthalene | HO-C(C≡CH)(4-OCF₃-C₆H₄)(4-CH₃O-C₆H₄) | 2-(4-OCF₃-phenyl)-2-(4-methoxyphenyl)-5-methyl-2H-naphtho[1,2-b]pyran | 16 |
| 31 | 4-hydroxy-3-methylnaphthalene | HO-C(C≡CH)(2-furyl)(3-F-4-CH₃O-C₆H₃) | 2-(2-furyl)-2-(3-fluoro-4-methoxyphenyl)-5-methyl-2H-naphtho[1,2-b]pyran | 10 |
| 32 | 4-hydroxy-3-methylnaphthalene | HO-C(C≡CH)(2-thienyl)(4-CH₃O-C₆H₄) | 2-(2-thienyl)-2-(4-methoxyphenyl)-5-methyl-2H-naphtho[1,2-b]pyran | 12 |

TABLE 3-continued
| Ex. No. | Starting material | | Product | Yield (%) |
| --- | --- | --- | --- | --- |
| | Naphthol derivative | Propargyl alcohol derivative | | |
| 33 | 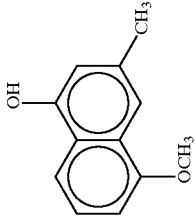 | 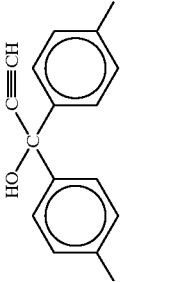 | 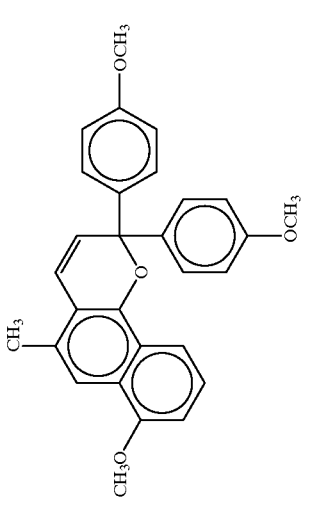 | 23 |
| 34 | 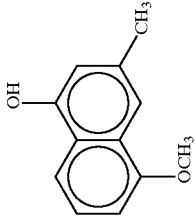 |  | 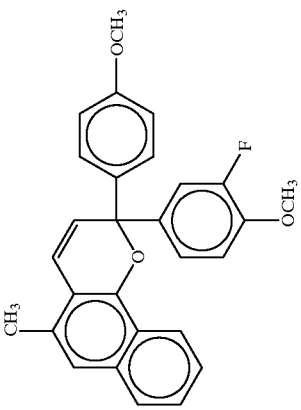 | 24 |
| 35 | 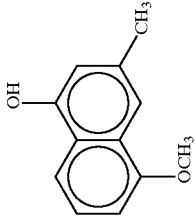 | 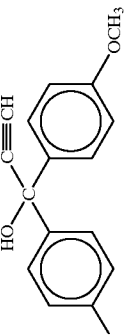 | 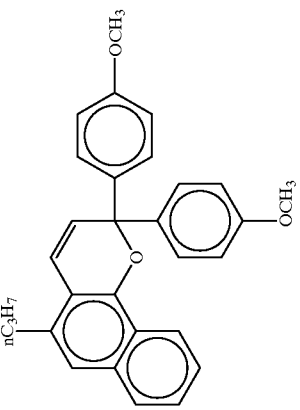 | 13 |

TABLE 3-continued

| Ex. No. | Starting material Naphthol derivative | Propargyl alcohol derivative | Product | Yield (%) |
|---|---|---|---|---|
| 36 | 3,6-dimethyl-naphthol | 1,1-bis(4-methoxyphenyl)-2-propyn-1-ol | chromene product | 25 |
| 37 | 3-methyl-6-phenyl-naphthol | 1,1-bis(4-methoxyphenyl)-2-propyn-1-ol | chromene product | 17 |
| 38 | 5-bromo-3-n-butyl-naphthol | 1,1-bis(3-fluoro-4-methoxyphenyl)-2-propyn-1-ol | chromene product | 9 |

TABLE 3-continued

| Ex. No. | Starting material | | Product | Yield (%) |
|---|---|---|---|---|
| | Naphthol derivative | Propargyl alcohol derivative | | |
| 39 | | | | 10 |
| 40 | | | | 8 |
| 41 | | | | 15 |

TABLE 4

| Ex. No. | Found C | H | O | Others | Calculated C | H | O | Others | 1H-NMR (ppm) |
|---|---|---|---|---|---|---|---|---|---|
| 27 | 75.66 | 4.96 | 10.83 | F: 8.55 | 75.68 | 4.95 | 10.81 | F: 8.56 | δ 5.9~9.0: 13H<br>δ 3.5~4.0: 6H<br>δ 1.5~2.0: 3H |
| 28 | 82.48 | 6.15 | 11.37 | | 82.46 | 6.16 | 11.38 | | δ 5.9~9.0: 15H<br>δ 3.5~4.0: 6H<br>δ 1.5~2.0: 5H |
| 29 | 82.55 | 6.43 | 11.02 | | 82.57 | 6.42 | 11.01 | | δ 5.9~9.0: 15H<br>δ 3.5~4.0: 4H<br>δ 1.5~2.0: 9H |
| 30 | 72.76 | 4.55 | 10.36 | F: 12.33 | 72.73 | 4.54 | 10.39 | F: 12.34 | δ 5.9~9.0: 15H<br>δ 3.5~4.0: 3H<br>δ 1.5~2.0: 3H |
| 31 | 77.74 | 4.95 | 12.41 | F: 4.91 | 77.72 | 4.92 | 12.44 | F: 4.92 | δ 5.9~9.0: 13H<br>δ 3.5~4.0: 3H<br>δ 1.5~2.0: 3H |
| 32 | 78.10 | 5.22 | 8.34 | S: 8.34 | 78.13 | 5.21 | 8.33 | S: 8.33 | δ 5.9~9.0: 14H<br>δ 3.5~4.0: 3H<br>δ 1.5~2.0: 3H |
| 33 | 79.42 | 5.96 | 14.62 | | 79.45 | 5.94 | 14.61 | | δ 5.9~9.0: 14H<br>δ 3.5~4.0: 9H<br>δ 1.5~2.0: 3H |
| 34 | 78.85 | 5.41 | 11.28 | F: 4.46 | 78.85 | 5.41 | 11.28 | F: 4.46 | δ 5.9~9.0: 14H<br>δ 3.5~4.0: 6H<br>δ 1.5~2.0: 3H |
| 35 | 82.54 | 6.44 | 11.02 | | 82.57 | 6.42 | 11.01 | | δ 5.9~9.0: 15H<br>δ 3.5~4.0: 6H<br>δ 1.5~2.0: 7H |
| 36 | 82.44 | 6.15 | 11.41 | | 82.46 | 6.16 | 11.38 | | δ 5.9~9.0: 14H<br>δ 3.5~4.0: 6H<br>δ 1.5~2.0: 6H |
| 37 | 84.35 | 5.74 | 9.93 | | 84.30 | 5.78 | 9.92 | | δ 5.9~9.0: 19H<br>δ 3.5~4.0: 6H<br>δ 1.5~2.0: 3H |
| 38 | 65.82 | 4.76 | 8.53 | F: 6.71<br>Br: 14.15 | 65.84 | 4.78 | 8.50 | F: 6.72<br>Br: 14.16 | δ 5.9~9.0: 12H<br>δ 3.5~4.0: 6H<br>δ 1.5~2.0: 9H |
| 39 | 84.44 | 6.44 | 9.12 | | 84.41 | 6.46 | 9.13 | | δ 5.9~9.0: 19H<br>δ 3.5~4.0: 5H<br>δ 1.5~2.5: 10H |
| 40 | 76.88 | 6.62 | 9.88 | S: 6.62 | 76.86 | 6.61 | 9.92 | S: 6.61 | δ 5.9~9.0: 12H<br>δ 3.5~4.0: 5H<br>δ 1.5~2.0: 15H |
| 41 | 78.03 | 5.22 | 11.56 | F: 4.71 | 78.00 | 5.25 | 12.00 | F: 4.75 | δ 5.9~9.0: 12H<br>δ 3.5~4.0: 3H<br>δ 1.5~2.0: 6H |

TABLE 5

| Ex. No. | Compound No. | λmax (nm) | Color density ε(120)−ε(0) | Fading rate t1/2 (min) | Change in the coloring degree ΔYI | Light resistance (%) |
|---|---|---|---|---|---|---|
| 42 | 1 | 462 | 0.7 | 3.6 | 0.2 | 99 |
| 43 | 3 | 488 | 1.1 | 3.1 | 2.0 | 95 |
| 44 | 4 | 470 | 0.7 | 2.4 | 5.0 | 80 |
| 45 | 5 | 465 | 0.6 | 2.2 | 1.5 | 99 |
| 46 | 6 | 480 | 0.8 | 2.8 | 1.8 | 97 |
| 47 | 7 | 468 | 0.8 | 3.5 | 1.7 | 96 |
| 48 | 8 | 490 | 0.7 | 2.2 | 2.0 | 92 |
| 49 | 9 | 500 | 0.6 | 2.2 | 2.2 | 94 |
| 50 | 10 | 465 | 0.6 | 3.2 | 1.5 | 93 |
| 51 | 11 | 485 | 1.0 | 3.4 | 1.9 | 97 |
| 52 | 12 | 476 | 0.9 | 6.8 | 1.0 | 99 |
| 53 | 13 | 500 | 0.8 | 3.3 | 1.5 | 97 |
| 54 | 14 | 492 | 0.8 | 4.3 | 1.3 | 99 |
| 55 | 15 | 486 | 0.9 | 4.8 | 1.2 | 96 |
| 56 | 16 | 470 | 0.9 | 5.2 | 1.2 | 99 |
| 57 | 17 | 452 | 0.7 | 3.2 | 0.7 | 98 |

TABLE 5-continued

|  | Compound No. | λmax (nm) | Color density ε(120)−ε(0) | Fading rate t1/2 (min) | Change in the coloring degree ΔYI | Light resistance (%) |
|---|---|---|---|---|---|---|
| 58 | 26 | 504 | 1.2 | 6.0 | 2.3 | 99 |
| 59 | 27 | 496 | 1.1 | 7.3 | 2.3 | 99 |
| 60 | 28 | 502 | 1.0 | 5.5 | 2.5 | 96 |
| 61 | 29 | 504 | 1.2 | 5.8 | 2.4 | 98 |
| 62 | 30 | 490 | 1.1 | 8.5 | 2.4 | 97 |
| 63 | 31 | 506 | 1.1 | 7.0 | 3.0 | 95 |
| 64 | 32 | 512 | 1.0 | 6.5 | 2.7 | 96 |
| 65 | 33 | 520 | 1.3 | 5.5 | 2.2 | 98 |
| 66 | 34 | 502 | 1.1 | 6.5 | 2.4 | 97 |
| 67 | 35 | 498 | 0.9 | 4.5 | 2.3 | 98 |
| 68 | 36 | 510 | 1.1 | 6.0 | 2.3 | 98 |
| 69 | 37 | 512 | 1.3 | 7.2 | 2.5 | 97 |
| 70 | 38 | 482 | 0.8 | 4.8 | 2.8 | 96 |
| 71 | 39 | 524 | 1.0 | 5.8 | 2.5 | 96 |
| 72 | 40 | 524 | 0.9 | 5.2 | 2.7 | 96 |
| 73 | 41 | 510 | 1.0 | 6.3 | 3.2 | 95 |
| Comp. Ex. No. | | | | | | |
| 1 | a | 492 | 1.3 | >30 | 2.5 | 97 |
| 2 | b | 488 | 1.2 | 14 | 6.5 | 80 |
| 3 | c | 484 | 1.3 | 20 | 2.4 | 96 |
| Ex. No. | | | | | | |
| 74 | 2 | 443 | 0.5 | 1.2 | 1.5 | 96 |
| 75 | 18 | 440 | 0.4 | 1.3 | 1.8 | 95 |
| 76 | 19 | 448 | 0.5 | 1.0 | 5.5 | 92 |
| 77 | 20 | 440 | 0.4 | 1.3 | 4.0 | 80 |
| 78 | 21 | 449 | 0.5 | 1.0 | 2.0 | 97 |
| 79 | 22 | 444 | 0.5 | 1.4 | 3.0 | 80 |
| 80 | 23 | 450 | 0.5 | 1.0 | 2.0 | 92 |
| 81 | 24 | 445 | 0.6 | 1.8 | 5.0 | 95 |
| 82 | 25 | 454 | 0.7 | 2.0 | 2.2 | 92 |
| Comp. Ex. No. | | | | | | |
| 4 | d | 452 | 1.0 | 11 | 1.5 | 98 |
| 5 | e | 456 | 0.6 | 4.0 | 5.5 | 96 |
| 6 | f | 446 | 0.6 | 4.1 | 6.0 | 96 |

TABLE 6

| Ex. No. | Component (A) (parts) | Component (B) (parts) | λ max (nm) | Initial color ε (0) | Color density ε (120)− ε (0) | Color-developing sensitivity | Fading rate t1/2 (min) | Durability (%) | Change in the color-ing degree ΔYI |
|---|---|---|---|---|---|---|---|---|---|
| 83 | AC1 (100) | BC1 (133) | 460 | 0.02 | 1.2 | 0.6 | 3 | 98 | 1.5 |
| 84 | AC1 (100) | BC1 (333) | 455 | 0.02 | 1.3 | 0.65 | 2.5 | 97 | 2.0 |
| 85 | AC1 (100) | BC1 (100) | 450 | 0.015 | 1.1 | 0.55 | 3.2 | 98 | 1.3 |
| 86 | AC1 (100) | BC1 (33) | 465 | 0.01 | 1.0 | 0.5 | 3.5 | 98 | 1.2 |
| 87 | AC1 (100) | BC1 (17) | 470 | 0.01 | 1.0 | 0.5 | 4.0 | 99 | 1.0 |
| 88 | AC2 (100) | BC1 (25) | 450 | 0.01 | 1.0 | 0.5 | 2.0 | 99 | 1.0 |
| 89 | AC3 (100) | BC2 (200) | 455 | 0.02 | 1.3 | 0.65 | 3.5 | 98 | 1.5 |
| 90 | AC4 (100) | BC2 (100) | 470 | 0.02 | 1.2 | 0.6 | 4.0 | 97 | 2.0 |
| 91 | AC1 (100) | BC1/BC3 (100) (67) | 455 | 0.01 | 1.0 | 0.5 | 2.0 | 96 | 2.2 |
| 92 | AC1 (100) | BC1/BC3 (142) (25) | 458 | 0.015 | 1.1 | 0.55 | 2.0 | 97 | 2.1 |
| 93 | AC1 (100) | BC1/BC3 (83) (83) | 452 | 0.01 | 1.0 | 0.5 | 2.0 | 95 | 2.3 |
| 94 | AC1 (100) | BC1/BC3 (133) (33) | 448 | 0.01 | 0.9 | 0.45 | 1.8 | 94 | 2.5 |

TABLE 6-continued

| | | | | | | | | | |
|---|---|---|---|---|---|---|---|---|---|
| 95 | AC2 (100) | BC1/BC4 (100) (66) | 460 | 0.02 | 1.2 | 0.6 | 3 | 98 | 1.5 |
| 96 | AC2 (100) | BC1/BC4 (21) (4) | 450 | 0.02 | 1.0 | 0.5 | 2.2 | 98 | 1.2 |
| 97 | AC3 (100) | BC2/BC3 (50) (50) | 450 | 0.015 | 1.1 | 0.55 | 3.5 | 96 | 1.8 |
| 98 | AC4 (100) | BC1/BC4 (100) (100) | 468 | 0.02 | 0.9 | 0.45 | 4.0 | 95 | 2.2 |
| 99 | AC1/AC2 (50) (50) | BC1 (250) | 455 | 0.02 | 1.1 | 0.55 | 2.8 | 98 | 1.5 |
| 100 | BC2/AC4 (33) (67) | BC2 (33) | 460 | 0.015 | 0.9 | 0.45 | 3.5 | 98 | 1.8 |
| 101 | AC1/AC3 (50) (50) | BC1/BC2/BC3 (30) (30) (40) | 455 | 0.01 | 0.9 | 0.45 | 2.5 | 95 | 2.1 |
| 102 | AC1 (100) | BC2/BC4/BC4 (160) (20) (20) | 458 | 0.02 | 1.0 | 0.5 | 2.6 | 97 | 1.6 |

| Comp. Ex. No. | Other Chromene Compound (parts) | λ max (nm) | Initial color ε (0) | Color density ε (120)– ε (0) | Color-developing sensitivity | Fading rate t½ (min) | Durability (%) | Change in the coloring degree ΔYI |
|---|---|---|---|---|---|---|---|---|
| 7 | C1 (100) | 450 | 0.01 | 1.0 | 0.2 | >10 | 90 | 2.0 |
| 8 | C2 (100) | 458 | 0.02 | 0.9 | 0.2 | 4.0 | 95 | 4.0 |
| 9 | C3 (100) | 480 | 0.01 | 1.0 | 0.2 | 10 | 95 | 5.0 |
| 10 | C4 (100) | 432 | 0.01 | 0.5 | 0.2 | 1.0 | 95 | 5.0 |

TABLE 7

| Ex. No. | Polymerizable monomer composition (parts) polymerization initiator (% by wt.) other additive (% by wt.) | λ max (nm) | Initial color ε (0) | Color density ε (120)– ε (0) | Color-developing sensitivity | Fading rate t½ (min) | Durability (%) | change in the coloring degree ΔYI |
|---|---|---|---|---|---|---|---|---|
| 103 | BPE-100N/3G/GMA/MS/MSD (50   30 10  9  1) perocta O/perbutyl ND = (0.4/0.5) | 460 | 0.02 | 1.2 | 0.5 | 3.2 | 98 | 1.0 |
| 104 | BPE-100N/3G/GMA/MS/MSD (50   30 10  9  1) perocta O/perbutyl ND = (0.4/0.5) sumisorb 110 = (0.04) | 460 | 0.02 | 1.2 | 0.5 | 3.2 | 98 | 0.6 |
| 105 | BPE-100N/3G/GMA/MS/MSD (50   30 10  9  1) perocta O/perbutyl ND = (0.4/0.5) tinubin P = (0.04) | 460 | 0.02 | 1.1 | 0.48 | 3.2 | 98 | 0.8 |
| 106 | 4G/3PG/GMA/MSD (45 45  9  1) perbutyl ND = (1.0) | 458 | 0.02 | 1.2 | 0.6 | 2.8 | 98 | 1.5 |

TABLE 8

| Ex. No. | Component (A) (parts) | Component (B) (parts) | Component (C) (parts) | Component (D) (parts) | Color tone after 30 sec | Color tone after 15 min | Coloring degree before aged YI (0) | Change in the coloring degree ΔYI |
|---|---|---|---|---|---|---|---|---|
| 107 | AC1 (0.025) | BC1 (0.025) | CO1 (0.05) | DF1 (0.05) | grey | grey | 14 | 2.0 |
| 108 | AC2 (0.05) | BC1 (0.02) | CO1 (0.05) | DF1 (0.05) | grey | grey | 14 | 1.5 |
| 109 | AC1 (0.05) | BC1 (0.015) | CO1 (0.04) | DF1 (0.03) | brown | brown | 13 | 1.5 |
| 110 | AC4 (0.02) | BC1/BC3 (0.02) (0.02) | CO1 (0.05) | DF1 (0.05) | grey | grey | 15 | 2.0 |
| 111 | AC1/AC2 (0.015) (0.03) | BC1 (0.02) | CO1 (0.05) | DF1 (0.05) | grey | grey | 13 | 1.5 |
| 112 | AC2/AC5 (0.04) (0.01) | BC1 (0.015) | CO1 (0.05) | DF1 (0.05) | grey | grey | 12 | 1.8 |
| 113 | AC1 (0.02) | BC1/BC3 (0.02) (0.01) | CO1 (0.06) | DF1 (0.04) | grey | grey | 13 | 1.5 |

TABLE 8-continued

| | | | | | | | | |
|---|---|---|---|---|---|---|---|---|
| 114 | AC1 (0.06) | BC1/BC3 (0.01) (0.01) | CO1 (0.03) | DF1 (0.03) | brown | brown | 15 | 1.6 |
| 115 | AC1/AC2 (0.04) (0.03) | BC1 (0.015) | CO1 (0.03) | DF1 (0.03) | grey | grey | 12 | 2.2 |
| 116 | AC2 (0.08) | BC1 (0.02) | CO1 (0.04) | DF4 (0.05) | grey | grey | 14 | 1.5 |
| 117 | AC1 (0.02) | BC1 (0.025) | CO1 (0.05) | DF1/DF4 (0.025) (0.025) | grey | grey | 15 | 2.0 |
| 118 | AC1 (0.06) | BC1 (0.015) | CO1 (0.05) | DF4 (0.05) | grey | grey | 14 | 2.5 |
| 119 | AC2/AC3 (0.05) (0.01) | BC1 (0.015) | CO1/CO2 (0.03) (0.02) | DF1 (0.05) | bluish grey | bluish grey | 14 | 2.0 |
| 120 | AC1 (0.025) | BC1 (0.025) | CO1/CO3 (0.03) (0.005) | DF1 (0.05) | grey | grey | 14 | 1.5 |
| 121 | AC1/AC2 (0.015) (0.02) | BC1/BC3 (0.02) (0.01) | CO1/CO4 (0.05) (0.005) | DF1 (0.05) | grey | grey | 14 | 1.5 |
| 122 | AC1 (0.05) | BC1/BC4 (0.015) (0.01) | CO1 (0.03) | DF1 (0.03) | brown | brown | 15 | 2.0 |
| 123 | AC2 (0.05) | BC2 (0.015) | CO1 (0.06) | DF1/DF2 (0.025) (0.025) | grey | grey | 13 | 1.5 |
| 124 | AC2/AC4 (0.04) (0.01) | BC1 (0.015) | CO1 (0.05) | DF1/DF3 (0.025) (0.025) | grey | grey | 12 | 1.8 |
| 125 | AC6 (0.025) | BC1 (0.02) | CO1 (0.05) | DF1 (0.05) | grey | grey | 13 | 1.5 |
| 126 | AC1/AC6 (0.01) (0.015) | BC1 (0.02) | CO1 (0.05) | DF1/DF3 (0.025) (0.025) | grey | grey | 14 | 2.0 |
| 127 | AC6 (0.06) | BC2 (0.015) | CO1 (0.03) | DF3/DF5 (0.03) (0.03) | brown | brown | 12 | 2.2 |

| Comp. Ex. No. | Other chromen Compound (parts) | Component (C) (parts) | Component (D) (parts) | Color tone after 30 sec | Color tone after 15 min | Coloring degree before aged YI (0) | Change in the coloring degree ΔYI |
|---|---|---|---|---|---|---|---|
| 11 | C1 (0.05) | CO1 (0.05) | DF1 (0.05) | blue | grey | 11 | 2.0 |
| 12 | C2 (0.05) | CO1 (0.05) | DF1 (0.05) | blue | brown | 11 | 5.0 |
| 13 | C3 (0.05) | CO1 (0.05) | DF1 (0.05) | blue | brown | 11 | 5.2 |
| 14 | C4 (0.05) | CO1 (0.05) | DF1 (0.05) | blue | blue | 10 | 6.0 |

What is claimed is:

1. A chromene compound represented by the following general formula (1),

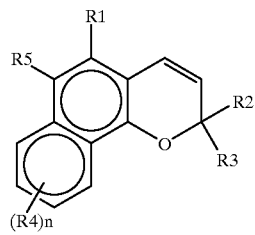

(1)

wherein
R1 is an alkyl group in which a carbon atom bonded to a naphthopyrane ring is a primary carbon atom, a secondary carbon atom or a tertiary carbon atom,
R2 and R3 are substituted or unsubstituted aryl groups or substituted or unsubstituted heteroaryl groups which may be different from each other, or R2 and R3 may be coupled to each other to form a substituted or unsubstituted adamantane ring, a substituted or unsubstituted bicyclononane ring, or a substituted or unsubstituted norbornane ring,
R4 is a substituent,
n is an integer of 0 to 4 representing the number of the substituents R4 and, when n is 2 or larger, R4 may be the same or different substituents,
R5 is a hydrogen atom or a substituent, and wherein when R1 is an alkyl group in which a carbon atom bonded to the naphthopyrane ring is a primary carbon atom, R2 and R3 may be each a group represented by the following formula (2),

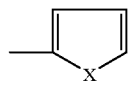

(2)

wherein X is an oxygen atom or a sulfur atom, or a group represented by the following formula (3),

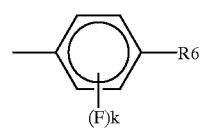

(3)

wherein R6 is an alkoxyl group or a trifluoromethoxy group, and k is 0 or 1,
and R2 and R3 may be different from each other, and at least either R2 or R3 is a group represented by the above formula (3),
R5 is a hydrogen atom.

2. A chromene compound represented by the following general formula (1'),

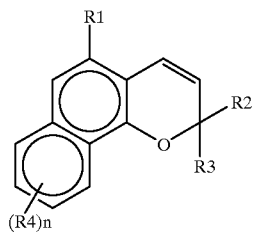

(1')

wherein
R1 is an alkyl group having 1 to 10 carbon atoms in which a carbon atom bonded to the naphthopyrane ring is a primary carbon atom,
R2 and R3 are groups represented by the following formula (2),

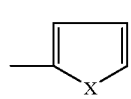

(2)

wherein X is an oxygen atom or a sulfur atom, or groups represented by the following formula (3),

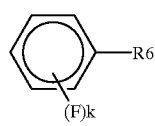

(3)

wherein R6 is an alkoxyl group or a trifluoromethoxy group, and k is 0 or 1, and R2 and R3 may be different from each other and at least either R2 or R3 is a group represented by the above formula (3),
R4 is a substituent, and
n is an integer of 0 to 4 representing the number of the substituents R4 and when n is not smaller than 2, R4 may be the same or different substituents.

3. A chromene compound according to claim 2, wherein R1 in the general formula (1') is an alkyl group having 1 to 4 carbon atoms in which a carbon atom bonded to the naphthopyrane ring is a primary carbon atom.

4. A chromene compound according to claim 2, wherein R1 in the general formula (1') is a methyl group or an ethyl group.

5. A chromene compound according to claim 2, wherein in the general formula (1'), R2 and R3 are both groups represented by the formula (3), R6 in the formula (3) is a methoxy group, an ethoxy group or a trifluoromethoxy group and when k=1, a fluorine atom is substituted for an ortho position relative to the group R6.

6. A chromene compound according to claim 2, wherein in the general formula (1'), R1 is a straight-chain alkyl group having 1 to 4 carbon atoms in which a carbon atom bonded to the naphthopyrane ring is a primary carbon atom, R2 and R3 are groups represented by the formula (2) or groups represented by the following formula (3'),

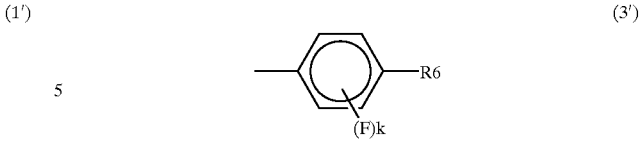

(3')

wherein R6 is a methoxy group, an ethoxy group or a trifluoromethoxy group, k is 0 or 1,
and R2 and R3 may be different from each other, and at least either one of R2 or R3 is a group represented by the above formula (3'), R4 is a group or an atom selected from is an alkyl group, an aryl group, an alkoxyl group, an aralkyl group and a halogen atom, n is an integer of 0 to 2 representing the number of the substituents R4 and when n is 2, R4 may be the same or different groups or atoms.

7. A chromene compound represented by the following general formula (1"),

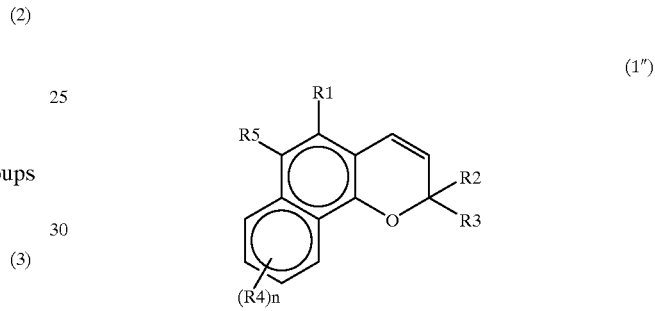

(1")

wherein
R1 is an alkyl group having 3 to 15 carbon atoms and in which a carbon atom bonded to the naphthopyrane ring is a secondary carbon atom or a tertiary carbon atom,
R2 and R3 are substituted or unsubstituted aryl groups or substituted or unsubstituted heteroaryl groups which may be different from each other, or R2 and R3 may be coupled to each other to form a substituted or unsubstituted adamantane ring, a substituted or unsubstituted bicyclononane ring or a substituted or unsubstituted norbornane ring,
R4 is a substituent,
n is an integer of 0 to 4 representing the number of the substituents R4 and when n is not smaller than 2, R4 may be the same or different substituents, and
R5 is a hydrogen atom or a substituent.

8. A chromene compound according to claim 7, wherein in the general formula (1"), R1 is an alkyl group having 3 to 6 carbon atoms in which a carbon atom bonded to the naphthopyrane ring is a secondary carbon atom or a tertiary carbon atom.

9. A chromene compound according to claims 7, wherein in the general formula (1"), R1 is an isopropyl group or a t-butyl group.

10. A chromene compound according to claim 7, wherein in the general formula (1"), R2 and R3 are aryl groups having 6 to 14 carbon atoms or heterocyclic groups having 4 to 12 carbon atoms, and each of the aryl groups having 6 to 14 carbon atoms or the heterocyclic groups having 4 to 12 carbon atoms may be substituted by at least one group or atom selected from the group consisting of:

an alkyl group having 1 to 4 carbon atoms;

an alkoxyl group having 1 to 4 carbon atoms;

an aralkyl group having 7 to 10 carbon atoms;

an alkylcarbonyl group having 2 to 7 carbon atoms;

an amino group having, as a substituent, an alkyl group with 1 to 10 carbon atoms or a hetero atom-containing alkyl group;

a substituted or unsubstituted heterocyclic group having a nitrogen atom as a hetero atom, and in which the nitrogen atom is bonded to the aryl group having 6 to 14 carbon atoms or to the heterocyclic group having 4 to 12 carbon atoms;

a condensed heterocyclic group formed by the condensation of the heterocyclic group with an aromatic hydrocarbon ring or an aromatic heterocyclic ring;

an aryl group having 6 to 14 carbon atoms; and a halogen atom.

11. A chromene compound according to claim 7, wherein R5 in the general formula (1") is a hydrogen atom.

12. A chromene compound according to claim 7, wherein in the general formula (1"), R1 is an alkyl group having 3 to 6 carbon atoms in which a carbon atom bonded to the naphthopyrane ring is a secondary carbon atom or a tertiary carbon atom, R2 and R3 are substituted or unsubstituted phenyl group which may be different from each other or are each a substituted or unsubstituted heteroaryl group selected from the group consisting of a furyl group, a pyryl group, a thienyl group and a benzothienyl group, R4 is a group selected from the group consisting of an alkyl group, an aryl group, an alkoxyl group, an acyloxy group and a hydroxyl group, n is 0 or 1, and R5 is a hydrogen atom.

13. A chromene compound according to claim 1, wherein the chromene compound is a 5-isopropyl-2,2-diphenyl-2H-benzo(h) chromene.

14. A chromene compound according to claim 1, wherein the chromene compound is a 5-t-butyl-2,2-diphenyl-2H-benzo(h) chromene.

15. A chromene compound according to claim 1, wherein the chromene compound is a 5-isopropyl-2,2-bis(3-fluoro-4-methoxyphenyl)-2H-benzo(h) chromene.

16. A chromene compound according to claim 1, wherein the chromene compound is a 5-methyl-2,2-bis(4-methoxyphenyl)-2H-benzo(h) chromene.

17. A chromene compound according to claim 1, wherein the chromene compound is a 5-isopropyl-2-(4-methoxyphenyl)-2-(4-trifluoromethoxyphenyl)-2H-benzo(h) chromene.

18. A chromene compound according to claim 1, wherein the chromene compound is a 5-isopropyl-2-phenyl-2-(4-trifluoromethoxyphenyl)-2H-benzo(h) chromene.

19. A photochromic material comprising a chromene compound of claim 1.

20. A photochromic polymerizable composition comprising 100 parts by weight of a polymerizable monomer and 0.001 to 10 parts by weight of a chromene compound of claim 1.

21. A photochromic polymerizable composition according to claim 20, wherein the polymerizable monomer comprises 100 parts by weight of a radically polymerizable monomer, and 1 to 30 parts by weight of a compound having at least one epoxy group in one molecule thereof and a radically polymerizable group.

22. A chromene composition comprising 100 parts by weight of a chromene compound represented by the following general formula (1),

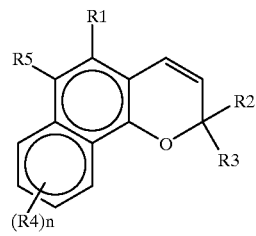

wherein

R1 is an alkyl group in which a carbon atom bonded to a naphthopyrane ring is a primary carbon atom, a secondary carbon atom or a tertiary carbon atom, R2, and R3 are substituted or unsubstituted aryl groups or substituted or unsubstituted heteroaryl groups which may be different from each other, or R2 and R3 may be coupled to each other to form a substituted or unsubstituted adamantane ring, a substituted or unsubstituted bicyclononane ring, or a substituted or unsubstituted norbornane ring, R4 is a substituent, n is an integer of 0 to 4 representing the number of the substituents R4 and, when n is 2 or larger, R4 may be the same or different substituents, R5 is a hydrogen atom or a substituent, and wherein when R1 is an alkyl group in which a carbon atom bonded to the naphthopyrane ring is a primary carbon atom, R2 and R3 may be each a group represented by the following formula (2),

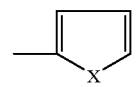

wherein X is an oxygen atom or a sulfur atom, or a group represented by the following formula (3),

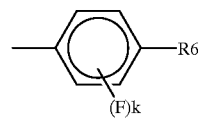

wherein R6 is an alkoxyl group or a trifuloromethoxy group, and k is 0 or 1, and R2 and R3 may be different from each other, and at least either R2 or R3 is a group represented by the above formula (3), and R5 is a hydrogen atom, and 10 to 1000 parts by weight of a chromene compound represented by the following general formula (7),

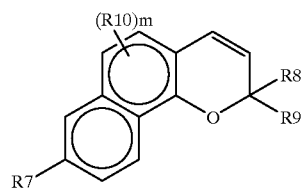

(7)

wherein

R7 is an amino group represented by the following general formula (8),

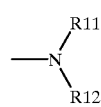

(8)

wherein R11 and R12 are hydrogen atoms, substituted or unsubstituted alkyl groups having 1 to 10 carbon atoms, substituted or unsubstituted aromatic hydrocarbon groups having 6 to 10 carbon atoms, or heterocyclic groups, which may be different from each other, or substituted or unsubstituted heterocyclic groups having a nitrogen atom as a hetero atom and in which the nitrogen atom is bonded to the naphthopyrane ring, or are condensed heterocyclic groups formed by the condensation of the heterocyclic groups with an aromatic hydrocarbon ring or an aromatic heterocyclic ring, R8 and R9 are substituted or unsubstituted aromatic hydrocarbon groups, substituted or unsubstituted aromatic heterocyclic groups, or alkyl groups, which may be different from each other, R10 is a substituent, m is an integer of 0 to 4 representing the number of the substituents R10 and when m is not smaller than 2, R10 may be the same or different groups.

23. A photochromic polymerizable composition comprising 100 parts by weight of a polymerizable monomer, and 0.001 to 10 parts by weight of a chromene composition of claim 22.

24. A photochromic polymerizable composition according to claim 23, wherein the polymerizable monomer contains 100 parts by weight of a radically polymerizable monomer, and 1 to 30 parts by weight of a compound containing at least one epoxy group and radically polymerizable groups in one molecule thereof.

25. A photochromic composition comprising 100 parts by weight of a chromene compound represented by the following general formula (1),

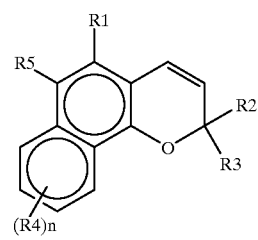

(1)

wherein

R1 is an alkyl group in which a carbon atom bonded to a naphthopyrane ring is a primary carbon atom, a secondary carbon atom or a tertiary carbon atom, R2 and R3 are substituted or unsubstituted aryl groups or substituted or unsubstituted heteroaryl groups which may be different from each other, or R2 and R3 may be coupled to each other to form a substituted or unsubstituted adamantane ring, a substituted or unsubstituted bicyclononane ring, or a substituted or unsubstituted norbornane ring, R4 is a substituent, n is an integer of 0 to 4 representing the number of the substituents R4 and, when n is 2 or larger, R4 may be the same or different substituents, R5 is a hydrogen atom or a substituent, and wherein when R1 is an alkyl group in which a carbon atom bonded to the naphthopyrane ring is a primary carbon atom, R2 and R3 may be each a group represented by the following formula (2),

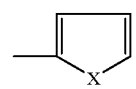

(2)

wherein X is an oxygen atom or a sulfur atom, or a group represented by the following formula (3),

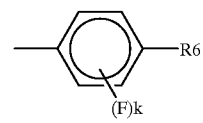

(3)

wherein R6 is an alkoxyl group or a trifuloromethoxy group, and k is 0 or 1, and R2 and R3 may be different from each other, and at least either R2 or R3 is a group represented by the above formula (3), and R5 is a hydrogen atom, 10 to 1000 parts by weight of a chromene compound represented by the following general formula (7),

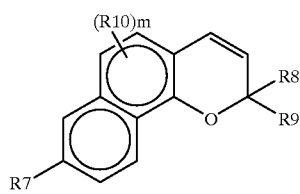

(7)

wherein
R7 is an amino group represented by the following general formula (8),

(8)

- wherein R11 and R12 are hydrogen atoms, substituted or unsubstituted alkyl groups having 1 to 10 carbon atoms, substituted or unsubstituted aromatic hydrocarbon groups having 6 to 10 carbon atoms, or heterocyclic groups, which may be different from each other,
- or substituted or unsubstituted heterocyclic groups having a nitrogen atom as a hetero atom and in which the nitrogen atom is bonded to the naphthopyrane ring, or are condensed heterocyclic groups formed by the condensation of the heterocyclic groups with an aromatic hydrocarbon ring or an aromatic heterocyclic ring,
- R8 and R9 are substituted or unsubstituted aromatic hydrocarbon groups, substituted or unsubstituted aromatic heterocyclic groups, or alkyl groups, which may be different from each other,
- R10 is a substituent,
- m is an integer of 0 to 4 representing the number of the substituents R10 and when m is not smaller than 2, R10 may be the same or different groups, 10 to 1000 parts by weight of a spirooxazine compound; and 10 to 1000 parts by weight of a fulgimide compound.

26. A photochromic polymerizable composition comprising 100 parts by weight of a polymerizable monomer, and 0.02 to 1 part by weight of a photochromic composition of claim 25.

27. A photochromic polymerizable composition according to claim 26, wherein the polymerizable monomer comprises 100 parts by weight of a radically polymerizable monomer, and 1 to 30 parts by weight of a compound containing at least one epoxy group and radically polymerizable groups in one molecule thereof.

28. A photochromic lens made of a polymer of a photochromic polymerizable composition of claim 26.

29. A chromene compound represented by the following general formula (1'),

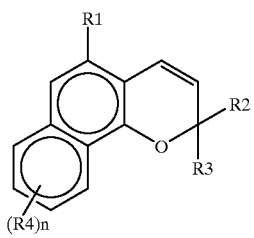

(1')

wherein
R1 is an alkyl group having 1 to 10 carbon atoms in which a carbon atom bonded to the naphthopyrane ring is a primary carbon atom,
R2 and R3 are groups represented by the following formula (2),

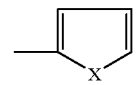

(2)

wherein X is an oxygen atom or a sulfur atom, or groups represented by the following formula (3),

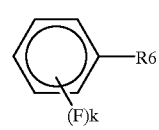

(3)

wherein either R2 or R3 is a group represented by the formula (2) and the other one of R2 and R3 is a group represented by the formula (3), R6 in the formula (3) is a methoxy group, an ethoxy group or a trifluoromethoxy group and k=0 or 1, and when k=1, a fluorine atom is substituted for an ortho position relative to the group R6,
R4 is a substituent, and
n is an integer of 0 to 4 representing the number of the substituents R4 and when n is not smaller than 2, R4 may be the same or different substituents.

30. A chromene compound represented by the following general formula (1),

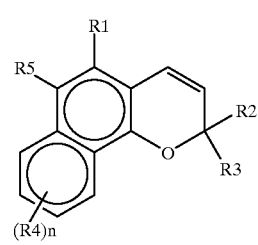

(1)

Wherein
R1 is an alkyl group having up to 10 carbon atoms in which a carbon atom bonded to a naphthopyrane ring is a primary carbon atom, a secondary carbon atom or a tertiary carbon atom,
R2 and R3 are substituted or unsubstituted aryl groups or substituted or unsubstituted heteroaryl groups which may be different from each other, R4 is a substituent, n is an integer of 0 to 4 representing the number of the substituents R4 and, when n is 2 or larger, R4 may be the same or different substituents, R5 is a hydrogen atom, and wherein when R1 is an alkyl group in which a carbon atom bonded to the naphthopyrane ring is a primary carbon atom, R2 and R3 may each be a group represented by the following formula (2),

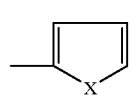

(2)

wherein X is an oxygen atom or a sulfur atom, or a group represented by the following formula (3),

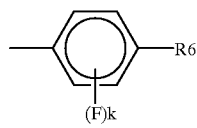

(3)

wherein R6 is an alkoxyl group or a trifluoromethoxy group, and k is 0 or 1, and R2 and R3 may be different from each other, and at least either R2 or R3 is a group represented by the above formula (2).

31. A chromene compound represented by the following general formula (1')

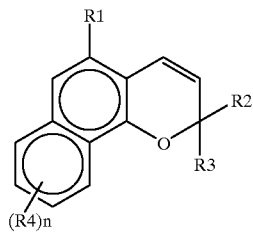

(1')

wherein

R1 is an alkyl group having 3 to 6 carbon atoms and in which a carbon atom bonded to the naphthopyrane ring is a secondary carbon atom or a tertiary carbon atom, R2 and R3 are groups represented by the following formula (2),

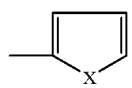

(2)

wherein X is an oxygen atom or a sulfur atom, or groups represented by the following formula (3),

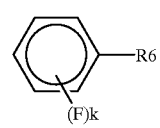

(3)

wherein R6 is an alkoxyl group or a trifluoromethoxy group, and k is 0 or 1, and R2 and R3 may be different from each other and at least either R2 or R3 is a group represented by the above formula (3), R4 is a substituent, and n is an integer of 0 to 4 representing the number of the substituents R4 and when n is not smaller than 2, R4 may be the same or different substituents.

32. A chromene compound according to claim 31, wherein in the general formula (1'), either R2 or R3 is a group represented by the formula (2) and the other one of R2 and R3 is a group represented by the formula (3), R6 in the formula (3) is a methoxy group, an ethoxy group or a trifluoromethoxy group and when k=1, a fluorine atom is substituted for an ortho position relative to the group R6.

* * * * *